United States Patent
Arnaiz et al.

(10) Patent No.: US 7,053,112 B2
(45) Date of Patent: May 30, 2006

(54) IMIDAZOLIDINEDIONE ANALOGS USEFUL AS ANTICOAGULANTS AND ANTITHROMBOTICS

(75) Inventors: Damian O. Arnaiz, Hercules, CA (US); Yuo-Ling Chou, Lafayette, CA (US); Brian D. Griedel, El Cerrito, CA (US); Raju Mohan, Encinitas, CA (US); Kenneth J. Shaw, Brookside, NJ (US)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/668,920

(22) Filed: Sep. 23, 2003

(65) Prior Publication Data

US 2004/0122073 A1   Jun. 24, 2004

Related U.S. Application Data

(60) Provisional application No. 60/413,067, filed on Sep. 24, 2002.

(51) Int. Cl.
  *C07D 231/04* (2006.01)
  *A61K 31/4166* (2006.01)

(52) U.S. Cl. ............ 514/392; 548/319.5; 548/320.1

(58) Field of Classification Search ............ 548/320.1, 548/319.5; 514/392
  See application file for complete search history.

(56) References Cited

U.S. PATENT DOCUMENTS

| | | | |
|---|---|---|---|
| 5,612,363 A * | 3/1997 | Mohan et al. | 514/392 |
| 6,034,238 A * | 3/2000 | Wehner et al. | 544/139 |
| 6,258,822 B1 * | 7/2001 | Geyer et al. | 514/275 |
| 6,284,796 B1 * | 9/2001 | Geyer et al. | 514/620 |
| 6,495,562 B1 * | 12/2002 | Bruncko et al. | 514/307 |
| 6,504,031 B1 * | 1/2003 | Bruncko et al. | 546/145 |
| 6,509,366 B1 * | 1/2003 | Rachwal et al. | 514/399 |
| 6,773,896 B1 * | 8/2004 | Chi et al. | 435/13 |
| 2001/0049374 A1 * | 12/2001 | Steele et al. | 514/275 |
| 2002/0168700 A1 | 11/2002 | Chi et al. | |

FOREIGN PATENT DOCUMENTS

WO    WO 9905096 A2 *  2/1999

OTHER PUBLICATIONS

The New Encyclopaedia Britannica, 15th ed. (1994), vol. 23, at p. 339 and pp. 398-401 ("Mammals," entry for order Lagomorpha (rabbits, hares, pikes)).*

* cited by examiner

*Primary Examiner*—Kamal A. Saeed
*Assistant Examiner*—Susannah L. Chung
(74) *Attorney, Agent, or Firm*—Jacqueline S. Larson; Ronald S. Hermenau

(57) ABSTRACT

A compound is disclosed, which is useful in treating a mammal having a disease-state characterized by thrombotic activity. The compound is of the following formula:

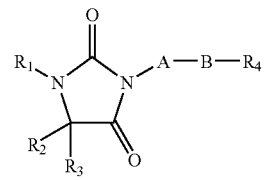

wherein A, B, $R_1$, $R_2$, $R_3$ and $R_4$ are as defined herein or an isomer or isomeric mixture thereof or a pharmaceutically acceptable salt thereof.

2 Claims, No Drawings

IMIDAZOLIDINEDIONE ANALOGS USEFUL AS ANTICOAGULANTS AND ANTITHROMBOTICS

This application claims priority to U.S. Provisional Application Ser. No. 60/413,067 filed Sep. 24, 2002, the entirety of which is incorporated herein by reference.

FIELD OF THE INVENTION

The present invention relates to imidazolidinedione analogs and their pharmaceutically acceptable salts, which are useful in treating disease states characterized by thrombotic activity. The present invention further relates to the use of imidazolidinedione analogs as antithrombotic and/or anticoagulant agents. Pharmaceutical compositions comprising the imidazolidinedione analogs and methods of use are also disclosed.

BACKGROUND OF THE INVENTION

Thrombotic diseases remain a major health care problem despite the tremendous progress made in understanding the molecular mechanisms of blood coagulation and pathogenesis of thrombosis and atherosclerosis. In fact, each year in the United States, approximately 1.5 million patients experience acute myocardial infarction and 5 million patients develop angina.

Generally, thrombosis occurs from an imbalance between prothrombotic and antithrombotic mechanisms. In principle, enhanced platelet activation, increased thrombin formation and blood coagulation or reduced fibrinolytic activity all could lead to thrombosis. Currently marketed antithrombotic drugs and the majority in development are designed to inhibit platelets or blood coagulation factors. Thrombolytic agents, such as streptokinase, and recombinant tissue-type plasminogen activator (tPA) and urokinase (uPA) are used mostly for acute myocardial infarction (Verstraete, M., *The fibrinolytic system: from Petri dishes to genetic engineering, Thromb Haemost* 74, 25–35 (1995); 2). These protein-based drugs are designed to be administered intravenously for rapid onset of action.

Fibrinolysis is a physiological mechanism to remove intravascular thrombus and maintain vascular patency. After a blood clot is formed in an injured vessel, the fibrinolytic system degrades the fibrin clot, restoring blood flow to vital organs and tissues. The fibrinolytic system consists of several proteases, namely tPA and uPA and plasminogen, which form an enzymatic cascade in which tPA and uPA convert plasminogen to plasmin, which in turn degrades fibrin.

The fibrinolytic enzymes of the fibrinolytic system are not only physiologically important in vascular homeostasis but can also cause unwanted effects such as bleeding and excessive vascular proteolysis. Therefore, tight regulation of the fibrinolytic system is typically achieved by activation of zymogens through limited proteolysis, controlled binding of plasminogen or plasmin to fibrin, and inactivation of proteases by serine protease inhibitors, and inactivation of plasmin binding sites on fibrin by the action of plasma carboxypeptidase B. A major challenge for thrombolytic therapy is to reduce the incidence of angiographic reocclusion. In fact, angiographic reocclusion is observed in about 30% of patients three months after successful thrombolysis for acute myocardial infarction. Reocclusion significantly affects recovery of left ventricular function and leads to a poorer long-term clinical outcome. Other approaches are therefore necessary to reduce coronary reocclusion.

The first enzyme in the blood clotting cascade consists of two distinct protein subunits: a catalytic subunit, Factor VIIa, also referred to as FVIIa, and an essential regulatory subunit, tissue factor, also referred to as TF. FVIIa is a soluble serine protease, bound with its cofactor TF, a cell-surface, integral-membrane protein, responsible for the conversion of Factor X to Factor Xa. Factor VIIa is the triggering enzyme of the blood clotting cascade in hemostasis and thrombosis and may play an important role in hypercoagulable states. Indeed, certain epidemiological studies have found elevated FVII coagulant activity to be an independent risk factor for heart disease.

The tissue factor (TF) coagulation pathway is initiated when circulating FVIIa encounters TF, a cell surface glycoprotein, as a result of vascular injury or pathological perturbation. TF-induced coagulation plays a primary role in hemostasis and also in the pathogenesis of various thrombotic disorders. A Factor VIIa that is modified to be inactivated such as an active site-blocked activated factor, can be used as an antithrombotic agent based on its ability to block binding of Factor VIIa to TF.

The Factor VIIa/TF complex is involved in the pathogenic mechanism in a variety of thrombotic diseases and the circulating level of TF is a risk factor for certain patients. Factor VIIa and TF play a unique role in vascular injury in maintaining hemostasis and initiating thrombosis. TF is expressed in the adventitia normally, but is upregulated and expressed inappropriately in the media and neointima in vascular disease. TF expression in atherosclerotic plaques is increased and shielded from the blood by a thin fibrous cap that may rupture to expose TF. Surgical interventions such as balloon angioplasty, stenting, or endarterectomy damage the vessel wall and expose underlying TF. In the atherosclerotic, lipid-rich, thin-walled plaque, spontaneous rupture or endothelial erosion leads to TF exposure and thrombosis resulting in unstable angina and myocardial infarction. TF can circulate in cell-derived microparticles, and circulating TF levels are elevated in unstable angina suggesting that this circulating TF may contribute to thrombus formation. Often cancer is associated with a hypercoagulable state attributed to overexpression of TF on tumor cells. This predisposes the patient to deep vein thrombosis, pulmonary embolism and low grade disseminated intravascular coagulation (DIC). DIC results in microvascular fibrin deposition contributing to multi-organ failure. Results from acute arterial injury models of thrombosis indicate that protein-based inhibitors of Factor VIIa/TF are effective antithrombotics with less bleeding compared to thrombin and FXa inhibitors. In addition, Factor VIIa/TF inhibition is superior to other anticoagulants (heparin, FXa inhibitor) in preventing neointimal thickening and vascular stenosis following balloon injury.

However, a class of compounds is needed that are useful in treating diseases characterized by thrombotic activity. Also, compounds are needed that inhibit the activity of certain enzymes in the coagulation cascade such as Factor VIIa in vivo that overcome the problems associated with prior compounds. In addition, a class of compounds is necessary that has increased potency allowing smaller dosages than the compounds known in the prior art to prevent thrombosis and atherosclerosis, and may further be utilized to prevent cancer invasion and chemotherapy-induced fibrosis.

SUMMARY OF THE INVENTION

The compounds of the invention are useful in treating disease states characterized by thrombotic activity and as antithrombotic and/or anticoagulant agents. Further, the compounds of the invention inhibit certain enzymes in the coagulation cascade, such as Factor VIIa/TF complex. The compounds of the invention comprise compounds of the formula I:

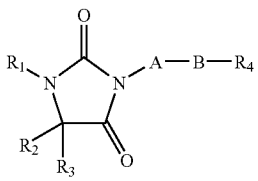

I wherein $R_1$ is selected from the group consisting of alkyl, alkenyl, alkynyl, aryl, carbocyclic, heterocyclic, heteroaryl and hydrogen;

$R_2$ and $R_3$ are each selected from the group consisting of alkyl, alkenyl, alkynyl, aryl, C-amido, carbocyclic, C-carboxy, heteroaryl, heterocyclic and hydrogen. $R_2$ and $R_3$ can also be combined to afford a carbocyclic group;

A is a branched or straight chain alkylene, a branched or straight chain alkylidene, a branched or straight chain alkylidyne, oxo, or sulfonyl;

B is aryl or heteroaryl; and $R_4$ is amidine, carboxyamidine, hydroxyamidine or ketoamidine.

It is presently a preferred feature of this invention that B is naphthalenyl and $R_4$ is amidine.

The invention further comprises methods of inhibiting Factor VIIa/TF by administration of the compounds of the invention to a mammal. The invention also comprises methods of treating coagulation disorders comprising administration of the compounds of the invention to a mammal. In another aspect, this invention provides compositions useful in treating a mammal having a disease-state characterized by thrombotic activity, which composition comprises a therapeutically effective amount of a compound of the invention as described above, or a pharmaceutically acceptable salt thereof, and a pharmaceutically acceptable excipient.

In another aspect, this invention provides a method of treating a mammal having a disease-state characterized by thrombotic activity, which method comprises administering to a mammal in need thereof a therapeutically effective amount of a compound of the invention as described above.

In another aspect, this invention provides a method of treating a mammal having a disease-state alleviated by the inhibition of certain enzymes in the coagulation cascade such as Factor VIIa/TF, which method comprises administering to a mammal in need thereof a therapeutically effective amount of a compound of the invention as described above.

In another aspect, this invention provides a method of inhibiting Factor VIIa/TF in vitro or in vivo by the administration of a compound of the invention.

DEFINITIONS

As used herein, unless specifically defined otherwise, the following terms have the meanings indicated.

An "acyl" group refers to a R'''C(=O)R'' wherein R''' is oxygen or nitrogen and R'' is alkenyl, alkyl, alkynyl, aryl, cycloalkyl, heteroaryl or hydrogen.

An "alkenyl" group refers to an alkyl group consisting of at least two carbon atoms and at least one carbon—carbon double bond.

An "alkyl" group refers to a saturated aliphatic hydrocarbon including straight chain and branched chain groups. Preferably, the alkyl group has from 1 to 20 carbon atoms. The alkyl group can be optionally substituted with one or more of the following groups: acyl, alkenyl, alkynyl, aryl, heteroaryl, carbocyclic, heterocyclic, carbonyl, halo, hydroxy, alkoxy, aryloxy, heteroaryloxy, nitro, trihalomethyl, C-amido, N-amido, C-carboxy, O-carboxy, N-carboxy, amino and $—NR_5R_6$.

An "alkylene" group refers to a branched or straight chain divalent hydrocarbon. Preferably, the alkylene group has from 1 to 6 carbon atoms.

An "alkylidene" group refers to an alkylene group consisting of at least two carbon atoms and at least one carbon—carbon double bond.

An "alkylidyne" group refers to an alkylene group consisting of at least two carbon atoms and at least one carbon—carbon triple bond.

An "alkynyl" group refers to an alkyl group consisting of at least two carbon atoms and at least one carbon—carbon triple bond.

An "alkoxy" group refers to an —O-alkyl, an —O-carbocyclic, an —O-alkenyl and an —O-alkynyl group, as defined herein.

An "amidine" group refers to $—C(=NH)NR_5R_6$ group where $R_5$ and $R_6$ are defined herein.

An "amino" group refers to a $—NR_5R_6$ group where $R_5$ and $R_6$ are hydrogen or alkyl.

An "aryl" group refers to an all-carbon monocyclic or fused-ring polycyclic group having a completely conjugated pi-electron system. Examples, without limitation, of aryl groups are phenyl, naphthalenyl and anthracenyl. The aryl group can be optionally and independently substituted with one or more of the following groups: acyl, alkyl, alkenyl, alkynyl, aryl, heteroaryl, carbocyclic, heterocyclic, carbonyl, halo, hydroxy, alkoxy, aryloxy, heteroaryloxy, nitro, trihalomethyl, C-amido, N-amido, C-carboxy, N-carboxy, O-carboxy, amidine, hydroxyamidine, ketoamidine, carboxyamidine, amino and $—NR_5R_6$.

An "aryloxy" group refers to both an —O-aryl and an —O-heteroaryl group, as defined herein.

A "C-amido" group refers to a $—C(=O)NR_5R_6$ group with $R_5$ and $R_6$ as defined herein.

A "carbocyclic" group refers to an all-carbon monocyclic or polycyclic fused ring group having 3–15 membered ring carbons wherein one or more of the rings can have one or more double bonds and one of the rings of a polycyclic fused ring group may be fully conjugated, with the proviso that a polycyclic fused ring group does not have a fully conjugated pi-electron system. Examples, without limitation, of carbocyclic groups are cyclopropane, cyclobutane, cyclopropane, cyclohexene, cyclohexadiene, dihydronaphthalene, tetrahydronaphthalene, and adamantane. The carbocyclic group can be optionally and independently substituted with one or more of the following groups: acyl, alkyl, alkenyl, alkynyl, aryl, heteroaryl, carbonyl, halo, hydroxy, alkoxy, aryloxy, heteroaryloxy, nitro, trihalomethyl, C-amido, N-amido, C-carboxy, N-carboxy, O-carboxy, amino, and $—NR_5R_6$ wherein $R_5$ and $R_6$ are defined herein.

A "carbonyl" group refers to a —C(=O)—R" group, where R" is hydrogen, alkyl, alkenyl, alkynyl, carbocyclic, aryl or heteroaryl.

A "carboxyamidine" group refers to —C(=NH)N(H)C(=O)OR$_5$ group where R$_5$ is defined herein.

A "C-carboxy" group refers to a —C(=O)O—R" where R" is hydrogen, alkyl, alkenyl, alkynyl, carbocyclic, aryl or heteroaryl.

A "halo" group refers to fluorine, chlorine, bromine or iodine.

A "heteroaryl" group refers to a monocyclic or polycyclic fused ring group having 3 to 15 ring membered carbon atoms wherein one or more of the ring carbon atoms can be independently replaced by nitrogen, oxygen or sulfur, and wherein said monocyclic or polycyclic fused ring group has a completely conjugated pi-electron system. Examples, without limitation, include pyrrole, imidazole, pyrazole, furan, thiophene, oxazole, pyridine, pyrimidine and quinoline. The heteroaryl group can be optionally and independently substituted with one or more of the following groups: acyl, alkyl, alkenyl, alkynyl, aryl, heteroaryl, carbocyclic, heterocyclic, carbonyl, halo, hydroxy, alkoxy, aryloxy, heteroaryloxy, nitro, trihalomethyl, C-amido, N-amido, C-carboxy, N-carboxy, O-carboxy, amidine, hydroxyamidine, ketoamidine, carboxyamidine, amino and —NR$_5$R$_6$.

A "heterocyclic" group refers to a monocyclic or polycyclic fused ring group having 3 to 15 ring membered carbon atoms wherein one or more of the ring carbon atoms can be independently replaced by nitrogen, oxygen or sulfur. The ring or rings may also have one or more double bonds, and one of the rings of a polycyclic fused ring group may be fully conjugated, with the proviso that the polycyclic fused ring group does not have a fully conjugated pi-electron system. The heterocyclic group can be optionally and independently substituted with one or more of the following groups: acyl, alkyl, alkenyl, alkynyl, aryl, heteroaryl, carbonyl, halo, hydroxy, alkoxy, aryloxy, heteroaryloxy, nitro, trihalomethyl, C-amido, N-amido, C-carboxy, O-carboxy, N-carboxy, amino and —NR$_5$R$_6$.

A "hydroxy" group refers to an —OH group.

A "hydroxyamidine" group refers to —C(=NH)N(H)OR$_5$ group where R$_5$ is defined herein.

A "ketoamidine" group refers to —C(=NH)N(H)C(=O)R$_5$ group where R$_5$ is defined herein.

An "N-amido" group refers to a —NR$_5$C(=O)R$_6$ group with R$_5$ and R$_6$ as defined herein.

An "N-carboxy" group refers to —NC$_x$(=O)OR" wherein R" is hydrogen alkyl, alkenyl, alkynyl, carbocyclic, heterocyclic, aryl, or heteroaryl and x is an integer from 2 to 4.

A "nitro" group refers to an —NO$_2$ group.

An "O-carboxy" group refers to a —OC$_x$(=O)OR" wherein R" is hydrogen, alkyl, alkenyl, alkynyl, carbocyclic, aryl or heteroaryl and x is an integer from 2 to 4.

An "oxo" group refers to —C$_x$(=O)—, wherein x represents an integer from 0–2.

A "sulfonyl" group refers to —S(=O)$_2$—.

A "trihalomethyl" group refers to a —CX$_3$ group wherein X is a halo group as defined herein.

As used herein, R$_5$ and R$_6$ are independently selected from hydrogen, alkyl, alkenyl, alkynyl, carbocyclic, heterocyclic, aryl or heteroaryl.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitutions.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids, such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts, which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betamine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethamine, dicyclohexylamine, choline and caffeine.

"Rt" refers to room temperature.

"Therapeutically effective amount" refers to that amount of a compound of formula (I) which, when administered to a mammal in need thereof, is sufficient to effect treatment, as defined below, for disease-states characterized by thrombotic activity. The amount of a compound of formula (I) which constitutes a "therapeutically effective amount" will vary depending on the compound, the disease-state and its severity, and the age of the mammal to be treated, but can be determined routinely by one of ordinary skill in the art having regard to his own knowledge and to this disclosure.

"Treating" or "treatment" as used herein cover the treatment of a disease-state in a mammal, which disease-state is characterized by thrombotic activity, and include:

(i) preventing the disease-state from occurring in a mammal, in particular, when such mammal is predisposed to the disease-state but has not yet been diagnosed as having it;

(ii) inhibiting the disease-state, i.e., arresting its development; or (iii) relieving the disease-state, i.e., causing regression of the disease-state.

The disease state may comprise unstable angina, myocardial infarction, cerebral thromboembolism, transient ischemic attack, stroke, DVT, and coronary reocclusion after thrombolytic therapy, as well as others.

The yield of each of the reactions described herein is expressed as a percentage of the theoretical yield.

The compounds of the invention, or their pharmaceutically acceptable salts, may have asymmetric carbon atoms, oxidized sulfur atoms or quaternized nitrogen atoms in their structure. The compounds of the invention and their pharmaceutically acceptable salts may therefore exist as isomers, such as single stereoisomers, racemates, and as isomeric mixtures, such as mixtures of enantiomers and diastereomers. All such isomers and isomeric mixtures thereof are intended to be within the scope of this invention. Resolution of the aforesaid compounds is known to those skilled in the art.

DETAILED DESCRIPTION OF THE PRESENTLY PREFERRED EMBODIMENTS

The compounds of the invention are inhibitors of Factor VIIa/TF and are useful as anticoagulants and in disease states characterized by thrombotic activity. The compounds of the invention comprise compounds of the formula I:

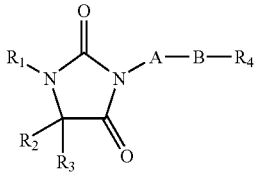

wherein $R_1$ is selected from the group consisting of alkyl, alkenyl, alkynyl, aryl, carbocyclic, heterocyclic, heteroaryl and hydrogen;

R2 and R3 are each selected from the group consisting of alkyl, alkenyl, alkynyl, aryl, C-amido, carbocyclic, C-carboxy, heteroaryl, heterocyclic and hydrogen. $R_2$ and $R_3$ can also be combined to afford a carbocyclic group;

A is a branched or straight chain alkylene, a branched or straight chain alkylidene, a branched or straight chain alkylidyne, oxo, or sulfonyl;

B is aryl or heteroaryl; and $R_4$ is amidine, carboxyamidine, hydroxyamidine or ketoamidine.

It is presently a preferred feature of this invention that B is naphthalenyl and $R_4$ is amidine.

The most preferred compounds of the invention are selected from the group consisting of:

1-[[7-(aminoiminomethyl)-2-naphthalenyl]methyl]-2,5-dioxo-4-phenyl-3-(phenylmethyl)-4-imidazolidineacetamide;

1-[[7-(aminoiminomethyl)-2-naphthalenyl]methyl]-2,5-dioxo-4-phenyl-3-(phenylmethyl)-4-imidazolidineacetic acid;

1-[[7-(aminoiminomethyl)-2-naphthalenyl]methyl]-2,5-dioxo-4-phenyl-3-(phenylmethyl)-4-imidazolidinepropanamide;

7-[[4-(4-aminophenyl)-4-methyl-2,5-dioxo-3-(phenylmethyl)-1-imidazolidinyl]methyl]-2-naphthalenecarboximidamide;

7-[[3-(4-aminophenyl)methyl)-4-methyl-2,5-dioxo-4-phenyl-1-imidazolidinyl]methyl]-2-naphthalenecarboximidamide;

7-[[4-(4-aminophenyl)-4-methyl-2,5-dioxo-3-(phenylmethyl)-1-imidazolidinyl]methyl]-2-naphthalenecarboximidamide;

4-[[3-[[7-(aminoiminomethyl)-2-naphthalenyl]methyl]-5-methyl-2,4-dioxo-5-phenyl-1-imidazolidinyl]methyl]-benzamide;

3-[[3-[[7-(aminoiminomethyl)-2-naphthalenyl]methyl]-5-methyl-2,4-dioxo-5-phenyl-1-imidazolidinyl]methyl]-benzamide;

7-[[3-[(3-aminophenyl)methyl]-4-methyl-2,5-dioxo-4-phenyl-1-imidazolidinyl]methyl]-2-naphthalenecarboximidamide; and 7-[[3-[[4-(aminoiminomethyl)phenyl]methyl]-4-methyl-2,5-dioxo-4-phenyl-1-imidazolidinyl]methyl]-2-naphthalene carboximidamide.

The invention further comprises methods of inhibiting Factor VIIa/TF by administration of the compounds of the invention to a mammal such as a human. The invention also comprises methods of treating coagulation disorders comprising administration of the compounds of the invention to a mammal. In another aspect, this invention provides compositions useful in treating a mammal having a disease-state characterized by thrombotic activity, which composition comprises a therapeutically effective amount of a compound of the invention as described above, or a pharmaceutically acceptable salt thereof, and a pharmaceutically acceptable excipient.

In another aspect, this invention provides a method of treating a mammal having a disease-state characterized by thrombotic activity, which method comprises administering to a mammal in need thereof a therapeutically effective amount of a compound of the invention as described above.

In another aspect, this invention provides a method of treating a mammal having a disease-state alleviated by the inhibition of Factor VIIa/TF, which method comprises administering to a mammal in need thereof a therapeutically effective amount of a compound of the invention as described above.

In another aspect, this invention provides a method of inhibiting Factor VIIa/TF in vitro or in vivo by the administration of a compound of the invention.

Administration of the compounds of the present invention in pure form or in an appropriate pharmaceutical composition, can be carried out via any of the accepted modes of administration or agents for serving similar utilities. Thus, the compounds of the invention can be administered, for example, orally, nasally, parenterally, topically, transdermally, or rectally, in the form of a solid, semi-solid, lyophilized powder or liquid dosage forms, such as via tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention and 99% to about 1% by weight of a suitable pharmaceutical excipient. Preferably, the composition will be about 5% to about 75% by weight of a compound(s) of the invention with the rest being suitable pharmaceutical excipients.

The preferred route of administration is oral, using a convenient daily dosage regimen, which can be adjusted according to the degree of severity of the disease state to be treated. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations, and any other like excipient that may be apparent to one having ordinary skill in the art.

Preferably, such compositions will take the form of capsule, caplet, or tablet and therefore will also contain a diluent such as lactose, sucrose, dicalcium phosphate, and other like diluents; a disintegrant such as croscarmellose sodium or derivatives thereof; a lubricant such as magnesium stearate and other like lubricants; and a binder such as starch, gum acacia, polyvinylpyrrolidine, gelatin, cellulose ether derivatives, and other like lubricants.

The compounds of the present invention may also be formulated into a suppository using, for example, about 0.5% to about 50% active ingredient disposed in a carrier that slowly dissolves within the body. For example, typical carrier materials may be polyethylene glycol (PEG), PEG 1000 (96%) and PEG 4000 (4%).

Liquid pharmaceutically administrable compositions can, for example, be prepared by dissolving, dispersing, etc. a compound(s) of the invention (about 5% to about 20%), and optional pharmaceutical adjuvants in a carrier, such as, for example, water, saline, aqueous dextrose, glycerol, ethanol and other like carriers, to form a solution or suspension.

If desired, a pharmaceutical composition of the invention may also contain minor amounts of auxiliary substances such as wetting or emulsifying agents, pH buffering agents, and antioxidants, such as citric acid, sorbitan monolaurate, triethanolamine oleate, butylated hydroxytoluene, etc.

Actual methods of preparing such dosage forms are known and are apparent, to those skilled in the art. For example, see *Remington's Pharmaceutical Sciences*, 18th Ed., (Mack Publishing Co., Easton, Pa., 1990). The composition to be administered will contain a therapeutically effective amount of a compound of the invention for treatment of a disease state alleviated by the inhibition of Factor VIIa/TF, in accordance with the teachings of this invention.

The compounds of the present invention are administered in a therapeutically effective amount which will vary depending upon a variety of factors, including the activity of the specific compound employed, the metabolic stability and length of action of the compound, the age, body weight, general health, sex, diet, mode and time of administration, rate of excretion, drug combination, the severity of the particular disease-states and the host undergoing therapy. Generally, a therapeutically effective daily dose is from about 0.14 mg to about 14.3 mg/kg of body weight per day of a compound of the present invention. Preferably, the pharmaceutical composition includes from about 0.7 mg to about 10 mg/kg of body weight per day. For example, for administration to a 70 kg person, the dosage would be about 10 mg to about 1.0 gram per day of a compound of the invention. More preferably, the pharmaceutical composition includes about 50 mg to about 700 mg per day of a compound of the present invention. Most preferably, the pharmaceutical composition includes about 100 mg to about 500 mg per day of a compound of the present invention.

EXAMPLES

The present invention will be further illustrated in the following, non-limiting examples. The examples are illustrative only and do not limit the claimed invention regarding the materials, conditions, process parameters and the like recited herein.

Example 1

The compounds of the invention can be prepared according to the following reaction scheme:

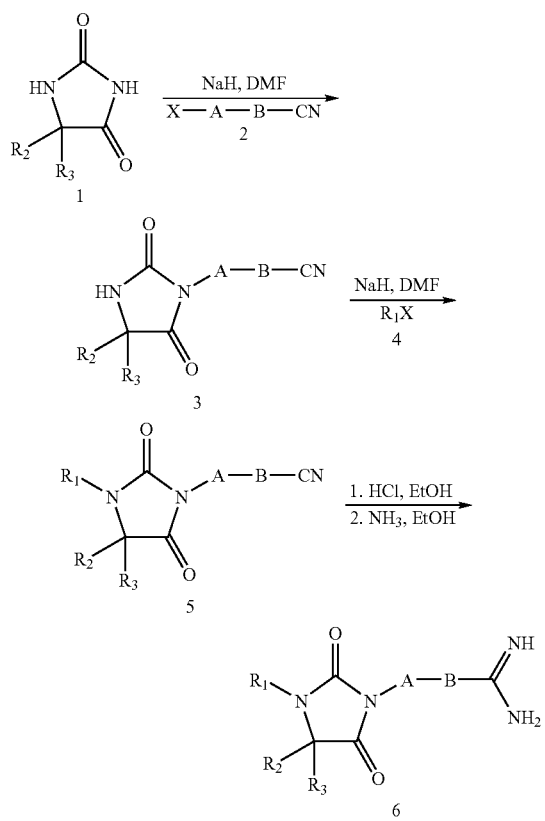

In the description of the synthesis methods in this Example 1, the definitions of $R_1$, $R_2$ and $R_3$, A and B are as defined in the Definitions herein, and x is a halogen.

Compounds of formula (1) can be prepared in accordance with methods known to those skilled in the art, such as by the method of Bucherer, Lieb., *J. Prak. Chem*. 1934, 141, 2, 5 and Melton, J. W.; Henze, H. R., *J. Am. Chem. Soc*. 1947, 2018. These compounds are also commercially available, for example, from Sigma-Aldrich, St. Louis, Mo. Compounds of formula (4) also can be prepared in accordance with methods known to those skilled in the art and are also commercially available from Sigma-Aldrich, St. Louis, Mo. Compounds of formulae (2) also can be prepared in accordance with methods known to those skilled in the art, such as the methods disclosed in European Published Patent Application 0 540 051, and are also commercially available from Sigma-Aldrich, St. Louis, Mo.

In general, compounds of formula (6) are prepared by first treating a compound of formula (1) in an aprotic solvent, preferably dimethylformamide, with a strong inorganic base, preferably sodium hydride. The resulting reaction mixture is stirred for 30 min. to 3 hr., preferably for 1 h at ambient temperature. A compound of formulae (2) is then added to the reaction mixture, and the resulting mixture is stirred for 1 to 24 hours, preferably 4 hours at ambient temperature. Isolation through conventional techniques, such as aqueous extraction and column chromatography, yields a compound of formula (3).

The compound of formula (3) is then dissolved in an aprotic solvent, preferably dimethylformamide, and treated with a strong inorganic base, preferably sodium hydride. The resulting reaction mixture is stirred for 30 min. to 3 hr., preferably for 1 h at ambient temperature. A compound of formulae (4) is then added to the reaction mixture, and the resulting mixture is stirred for 1 to 24 hours, preferably 4 hours at ambient temperature. Isolation through conventional techniques, such as aqueous extraction and column chromatography yields a compound of formula (5).

The compound of formula (5) is then dissolved in an anhydrous alkanol, preferably ethanol and the resulting solution is then treated with an anhydrous mineral acid, preferably HCl, while maintaining the reaction temperature between about −78° C. and ambient temperature for between 2 hours to 24 hours, and allowing the temperature to rise to ambient temperature while monitoring for reaction completion, for example, through reverse phase HPLC. The solvent is then removed and the resulting residue dissolved in fresh anhydrous alkanol, preferably ethanol. The resulting solution is then treated with anhydrous ammonia at ambient pressure or in a sealed flask, at temperatures from between ambient temperature and 100° C., for about 1 to about 5 hours. The compound of formula (6) is then isolated by standard techniques, such as concentration and reverse phase HPLC.

Alternatively, instead of treating the resulting solution above with anhydrous ammonia, the resulting solution is treated with a compound of the formula —NH$_2$OR$_5$ to prepare the corresponding compound of formula (I) wherein R$_4$ is —C(NH)N(H)OR$_5$.

Hydrolysis under acidic conditions of the compounds of formula (6), wherein R$_1$, R$_2$ or R$_3$ independently contains —C(O)N(R$_5$)(R$_6$) or —C(O)OR$_6$ results in compounds of formula (6) wherein R$_1$, R$_2$ or R$_3$ independently contains —C(O)OR$_6$ wherein R$_6$ is hydrogen.

A preferred compound of the invention, 3-[[3-[[7-(aminoiminomethyl)-2-naphthalenyl]methyl]-5-methyl-2,4-dioxo-5-phenyl-1-imidazolidinyl]methyl]-benzamide, was synthesized as follows:

5-methyl-5-phenyl-2,4-imidazolidenedione commercially available from Sigma-Aldrich, St. Louis, Mo., (1.9 g, 10 mmol) was dissolved in dry DMF (100 mL) and then treated with 60% sodium hydride (400 mg, 10 mmol). After 3 h, 7-(bromomethyl)-2-naphthalene carbonitrile, prepared according to the methods disclosed in European Published Patent Application 0 540 051, (2.5 g, 10 mmol) was added as a solution in DMF (10 mL). The reaction mixture was stirred for 14 h. Then, the reaction mixture was partitioned between water (500 mL) and ethyl acetate (500 mL). The organic layer was washed with brine (200 mL), dried (MgSO$_4$) and concentrated to afford an oil. Chromatography (SiO$_2$) with hexane/ethyl acetate afforded 7-[[4-methyl-2,5-dioxo-4-phenyl-1-imidazolidinyl]methyl]-2-naphthalene carbonitrile.

7-[[4-methyl-2,5-dioxo-4-phenyl-1-imidazolidinyl]methyl]-2-naphthalene carbonitrile (200 mg, 0.56 mmol) was dissolved in DMF (20 mL) and then treated with 60% sodium hydride (75 mg, 0.56 mmol). The reaction mixture was stirred for 3 h and then treated with methyl 3-(bromomethyl)benzoate (130 mg, 0.56 mmol). The resulting reaction mixture was stirred for 14 h. Then, the reaction mixture was partitioned between water (100 mL) and ethyl acetate (100 mL). The organic layer was washed with brine (50 mL), dried (MgSO$_4$) and concentrated to afford 3-[[3-[(7-cyano)-2-naphthalenyl]methyl]-5-methyl-2,4-dioxo-5-phenyl-1-imidazolidinyl]methyl]-benzoic acid methyl ester. HCl was bubbled into a slurry of 3-[[3-[(7-cyano)-2-naphthalenyl]methyl]-5-methyl-2,4-dioxo-5-phenyl-1-imidazolidinyl]methyl]-benzoic acid methyl ester and methanol (10 mL) cooled in a dry ice/acetone bath. After the solution was saturated, the reaction flask was sealed and the temperature maintained at 5° C. for 16 hours. The solvent was removed in vacuo. The residue was dissolved in methanol (10 mL). The solution was cooled in a dry ice/acetone bath and ammonia (g) was bubbled in. The reaction flask was sealed then heated at 80° C. for 4 hours. The solvent was removed. The mixture was purified by HPLC on a C$^{18}$ Dynamax column with a 2–40% acetonitrile in water gradient with 0.1% trifluoroacetic acid to afford 3-[[3-[[7-(aminoiminomethyl)-2-naphthalenyl]methyl]-5-methyl-2,4-dioxo-5-phenyl-1-imidazolidinyl]methyl]-benzamide trifluoroacetate salt, $^1$H NMR (300 MHz, DMSO) δ 1.60 (s, 3H), 4.40 (AB quartet, 2H), 4.86 (s, 2H), 7.18–7.35 (m, 7H), 7.60 (d, 1H), 7.65–7.80 (m, 3H), 7.85 (s, 1H), 8.00 (d, 1H), 8.04 (d, 1H), 8.42 (s, 1H), 9.00 (s, 2H), 9.40 (s, 2H).

Example 2

In a similar manner, the following compounds were made as a trifluoroacetate salt. The $^1$H NMR characterization information follows each compound name:

1. 7-[(4-methyl-2,5-dioxo-4-phenyl-1-imidazolidinyl)methyl]-2-naphthalenecarboximidamide $^1$H NMR (300 MHz, DMSO) δ 1.68 (s, 3H), 4.75 (s, 2H), 7.22–7.38 (m, 3H), 7.42 (d, 2H), 7.58 (d, 1H), 7.75 (d, 1H), 7.80 (s, 1H), 7.95 (d, 1H), 8.05 (d, 1H), 8.38 (s, 1H), 9.04 (s, 3H), 9.38 (s, 2H).

2. 7-[[3-[[4-(aminoiminomethyl)phenyl]methyl]-2,5-dioxo-1-imidazolidinyl]methyl]-2-naphthalene carboximidamide $^1$H NMR (300 MHz, DMSO) δ 4.00 (s, 2H), 4.60 (s, 2H), 4.78 (s, 2H), 7.50 (d, 2H), 7.60 (d, 1H), 7.72–7.79 (m, 3H), 7.92–8.00 (m, 2H), 8.05 (d, 1H), 8.41 (s, 1H), 8.95 (s, 2H), 9.04 (s, 2H), 9.13 (s, 2H), 9.39 (s, 2H).

3. 7-[[3-[[4-(aminoiminomethyl)phenyl]methyl]-4-methyl-2,5-dioxo-4-phenyl-1-imidazolidinyl]methyl]-2-naphthalene carboximidamide $^1$H NMR (300 MHz, DMSO) δ 1.75 (s, 3H), 4.42 (AB quartet, 2H), 4.88 (s, 2H), 7.22–7.38 (m, $^5$H), 7.43 (d, 2H), 7.60 (d, 1H), 7.68 (d, 2H), 7.80 (d, 1H), 7.92 (s, 1H), 8.02 (d, 1H), 8.08 (d, 1H), 8.40 (s, 1H), 8.89 (s, 2H), 8.95 (s, 2H), 9.22 (s, 2H), 9.40 (s, 2H).

4. 7-[[4-methyl-2,5-dioxo-4-phenyl-3-(phenylmethyl)-1-imidazolidinyl]methyl]-2-naphthalene carboximidamide $^1$H NMR (300 MHz, DMSO) δ 1.60 (s, 3H), 4.36 (AB quartet, 2H), 4.83 (s, 2H), 7.10–7.38 (m, $^{10}$H), 7.60 (d, 1H), 7.79 (d, 1H), 7.90 (s, 1H), 8.02 (d, 1H), 8.09 (d, 1H), 8.40 (s, 1H), 9.03 (s, 2H), 9.40 (s, 2H).

5. 4-[[3-[[7-(aminoiminomethyl)-2-naphthalenyl]methyl]-5-methyl-2,4-dioxo-5-phenyl-1-imidazolidinyl]methyl]-benzoic acid $^1$H NMR (300 MHz, DMSO) δ 1.65 (s, 3H), 4.40 (AB quartet, 2H), 4.84 (s, 2H), 7.18–7.36 (m, $^8$H), 7.60 (d, 1H), 7.78 (d, 2H), 7.90 (s, 1H), 8.02 (d, 1H), 8.08 (d, 1H), 8.40 (s, 1H), 9.00 (s, 2H), 9.40 (s, 2H).

6. 3-[[3-[[7-(aminoiminomethyl)-2-naphthalenyl]methyl]-5-methyl-2,4-dioxo-5-phenyl-1-imidazolidinyl]methyl]-benzoic acid $^1$H NMR (300 MHz, DMSO) δ 1.70 (s, 3H), 4.42 (AB quartet, 2H), 4.90 (s, 2H), 7.20–7.40 (m, $^7$H), 7.62 (d, 1H), 7.78–7.83 (m, 3H), 7.93 (s, 1H), 8.05 (d, 1H), 8.12 (d, 1H), 8.40 (s, 1H), 9.06 (s, 2H), 9.40 (s, 2H).

7. 3-[[7-(aminoiminomethyl)-2-naphthalenyl]methyl]-5-methyl-2,4-dioxo-5-phenyl-1-imidazolidinepropanamide $^1$H NMR (300 MHz, DMSO) δ 1.80 (s, 3H), 2.25–2.40 (m, 2H), 3.04–3.20 (m, 1H), 3.40–3.60 (m, 1H), 4.80 (s, 2H), 7.20–7.40 (m, $^5$H), 7.58 (d, 1H), 7.76 (d, 1H), 7.85 (s, 1H), 8.04 (d, 1H), 8.10 (d, 1H), 8.40 (s, 1H), 9.04 (s, 2H), 9.40 (s, 2H).

8. 3-[[7-(aminoiminomethyl)-2-naphthalenyl]methyl]-5-methyl-2,4-dioxo-5-phenyl-1-imidazolidinepropanoic acid ethyl ester $^1$H NMR (300 MHz, DMSO) δ 1.05 (t, 3H), 1.80 (s, 3H), 2.35–2.45 (m, 2H, partially obscured by DMSO), 3.20–3.38 (m, 1H), 3.50–3.60 (m, 1H), 3.93 (q, 2H), 4.80 (s, 2H) 7.20–7.40 (m, $^5$H), 7.60 (d, 1H), 7.78 (d, 1H), 7.88 (s, 1H), 8.03 (d, 1H), 8.10 (d, 1H), 8.40 (s, 1H), 9.08 (s, 2H), 9.40 (s, 2H).

9. 7-[[4-methyl-3-[(3-nitrophenyl)methyl]-2,5-dioxo-4-phenyl-1-imidazolidinyl]methyl]-2-naphthalenecarboximidamide $^1$H NMR (300 MHz, DMSO) δ 1.78 (s, 3H), 4.58 (AB quartet, 2H), 4.90 (s, 2H), 7.10–7.30 (m, $^5$H), 7.44 (t, 1H), 7.60 (d, 2H), 7.78 (d, 1H), 7.80–8.25 (m, $^5$H), 8.40 (s, 1H), 9.08 (s, 2H), 9.40 (s, 2H).

10. 7-[[3-[(3-aminophenyl)methyl]-4-methyl-2,5-dioxo-4-phenyl-1-imidazolidinyl]methyl]-2-naphthalenecarboximidamide $^1$H NMR (300 MHz, DMSO) δ 1.70 (s, 3H), 4.40 (AB quartet, 2H), 4.85 (s, 2H), 7.15–7.40 (m, $^9$H), 7.60 (d, 1H), 7.80 (d, 1H), 7.92 (s, 1H), 8.04 (d, 1H), 8.10 (d, 1H), 8.40 (s, 1H), 9.08 (s, 2H), 9.40 (s, 2H).

11. 7-[[2,5-dioxo-4,4-diphenyl-1-imidazolidinyl]methyl]-2-naphthalenecarboximidamide $^1$H NMR (300 MHz, DMSO) δ 4.83 (s, 2H), 7.30–7.40 (m, $^{10}$H), 7.60 (d, 1H), 7.80 (d, 1H), 7.85 (s, 1H), 8.00 (d, 1H), 8.06 (d, 1H), 8.38 (s, 1H), 9.05 (s, 2H), 9.40 (s, 2H), 9.78 (s, 1H).

12. 7-[[2,5-dioxo-4,4-dimethyl-1-imidazolidinyl]methyl]-2-naphthalenecarboximidamide $^1$H NMR (300 MHz, DMSO) δ 1.30 (s, $^6$H), 4.75 (s, 2H), 7.60 (d, 1H), 7.80 (d, 1H), 7.82 (s, 1H), 8.04 (d, 1H), 8.10 (d, 1H), 8.42 (s, 1H), 8.48 (s, 1H), 9.12 (s 2H), 9.40 (s, 2H).

13. 7-[[2,5-dioxo-3',4'-dihydro-1'H-spiro[imidazolidine-4,2-naphthalen]-1-yl]methyl]-2-naphthalenecarboximidamide $^1$H NMR (300 MHz, DMSO) δ 1.80–2.10 (m, 2H), 2.92 (s, 2H), 3.00 (dd, 2H), 7.00–7.18 (m, $^4$H), 7.60 (d, 1H), 7.80 (d, 1H), 7.90 (s, 1H), 8.03 (d, 1H), 8.12 (d, 1H), 8.48 (s, 1H), 8.75 (s, 1H), 9.06 (s, 2H), 9.40 (s, 2H).

14. 3-[[7-(aminoiminomethyl)-2-naphthalenyl]methyl]-5-methyl-2,4-dioxo-5-phenyl-1-imidazolidinepropanoic acid $^1$H NMR (300 MHz, DMSO) δ 1.80 (s, 3H), 2.30–2.50 (m, 2H, partially obscured by water), 3.10–3.22 (m, 1H), 3.43–3.50 (m, 1H), 4.80 (s, 2H), 7.13–7.22 (m, $^5$H), 7.60 (d, 1H), 7.78 (d, 1H), 7.85 (s, 1H), 8.03 (d, 1H), 8.10 (d, 1H), 8.40 (s, 1H), 9.08 (s, 2H), 9.40 (s, 2H).

15. 3-[[3-[[7-(aminoiminomethyl)-2-naphthalenyl]methyl]-5-methyl-2,4-dioxo-5-pheny-1-imidazolidinyl]methyl]-benzoic acid methyl ester $^1$H NMR (300 MHz, DMSO) δ 1.68 (s, 3H), 3.78 (s, 3H), 4.02 (AB quartet, 2H), 4.88 (s, 2H), 7.18–7.38 (m, $^7$H), 7.43 (d, 1H), 7.62 (d, 1H), 7.72–7.84 (m, 2H), 7.82 (s, 1H), 8.04 (d, 1H), 8.10 (d, 1H), 8.42 (s, 1H), 9.08 (s, 2H), 9.40 (s, 2H).

16. 4-[[3-[[7-(aminoiminomethyl)-2-naphthalenyl]methyl]-5-methyl-2,4-dioxo-5-phenyl-1-imidazolidinyl]methyl]-benzamide $^1$H NMR (300 MHz, DMSO) δ 1.60 (s, 3H), 4.38 (AB quartet, 2H), 4.85 (s, 2H), 7.08–7.40 (m, $^7$H), 7.60 (d, 1H), 7.65–7.80 (m, 3H), 7.86 (s, 1H), 7.96 (d, 1H), 8.02 (d, 1H), 8.37 (s, 1H), 8.98 (s, 2H), 9.38 (s, 2H).

17. 3-[[3-[[7-(aminoiminomethyl)-2-naphthalenyl]methyl]-5-methyl-2,4-dioxo-5-pheny-1-imidazolidinyl]methyl]-benzamide $^1$H NMR (300 MHz, DMSO) δ 1.60 (s, 3H), 4.40 (AB quartet, 2H), 4.86 (s, 2H), 7.18–7.35 (m, $^7$H), 7.60 (d, 1H), 7.65–7.80 (m, 3H), 7.85 (s, 1H), 8.00 (d, 1H), 8.04 (d, 1H), 8.42 (s, 1H), 9.00 (s, 2H), 9.40 (s, 2H).

18. 7-[[2,5-dioxo-4,4-diphenyl-3-(4-pyridinylmethyl)-1-imidazolidinyl]methyl]-2-naphthalenecarboximidamide $^1$H NMR (300 MHz, DMSO) δ 5.00 (s, 2H), 5.08 (s, 2H), 7.20–7.35 (m, $^{10}$H), 7.45 (d, 2H), 7.56 (d, 1H), 7.78 (d, 1H), 7.83 (s, 1H), 7.98 (d, 1H), 8.08 (d, 1H), 8.31 (s, 1H), 8.55 (d, 2H), 9.10 (s, 2H), 9.40 (s, 2H).

19. 7-[[2,5-dioxo-4,4-diphenyl-3-(3-pyridinylmethyl)-1-imidazolidinyl]methyl]-2-naphthalenecarboximidamide $^1$H NMR (300 MHz, DMSO) δ 4.80–5.00 (m, $^4$H), 7.18–7.30 (m, $^{10}$H), 7.52 (d, 1H), 7.68 (dd, 1H), 7.75–7.80 (m, 2H), 7.94 (d, 2H), 8.05 (d, 1H), 8.30 (d, 2H), 8.58 (d, 1H), 9.05 (s, 2H), 9.40 (s, 2H).

20. 7-[[3-[[4-(dimethylamino)phenyl]methyl]-2,5-dioxo-4,4-diphenyl-1-imidazolidinyl]methyl]-2-naphthalenecarboximidamide $^1$H NMR (300 MHz, DMSO) δ 3.00 (s, $^6$H), 4.65 (s, 2H), 4.95 (s, 2H), 6.83 (d, 2H), 7.17–7.38 (m, $^{12}$H), 7.56 (d, 1H), 7.78–7.82 (m, 2H), 7.98 (d, 1H), 8.06 (d, 1H), 8.30 (s, 1H), 9.10 (s, 2H), 9.40 (s, 2H).

21. 7-[[3-[[5-(dimethylamino)-2-methoxy-phenyl]methyl]-2,5-dioxo-4,4-diphenyl-1-imidazolidinyl]methyl]-2-naphthalenecarboximidamide $^1$H NMR (300 MHz, DMSO) δ 2.90 (s, $^6$H), 3.60 (s, 3H), 4.60 (s, 2H), 5.00 (s, 2H), 6.80 (d, 2H), 7.10–7.40 (m, 1H), 7.58 (d, 1H), 7.78–7.84 (m, 2H), 7.98 (d, 1H), 8.05 (d, 1H), 8.24 (s, 1H), 9.04 (s, 2H), 9.39 (s, 2H).

22. 7-[[3-[3-(dimethylamino)-phenyl]methyl]-2,5-dioxo-4,4-diphenyl-1-imidazolidinyl]methyl]-2-naphthalenecarboximidamide $^1$H NMR (300 MHz, DMSO) δ 2.95 (s, $^6$H), 4.70 (s, 2H), 4.98 (s, 2H), 6.88 (d, 1H), 7.03 (s, 1H), 7.10–7.33 (m, $^{12}$H), 7.55 (d, 1H), 7.75–7.83 (m, 2H), 7.96 (d, 1H), 8.05 (d, 1H), 8.30 (s, 1H), 9.10 (s, 2H), 9.40 (s, 2H).

23. 7-[[[4-(4-hydroxyphenyl)]-2,5-dioxo-4-phenyl-1-imidazolidinyl]methyl]-2-naphthalenecarboximidamide $^1$H NMR (300 MHz, DMSO) δ 4.83 (s, 2H), 6.75 (d, 2H), 7.10 (d, 2H), 7.25–7.40 (m, $^5$H), 7.58 (d, 1H), 7.80 (d, 1H), 7.84 (s, 1H), 8.00 (d, 1H), 8.08 (s, 1H), 8.38 (s, 1H), 9.07 (s, 2H), 9.40 (s, 2H), 9.62 (s, 1H).

24. 7-[[4-[4-(1H-imidazol-1-yl)phenyl]-4-methyl-2,5-dioxo-3-(phenylmethyl)-1-imidazolidinyl]methyl]-2-naphthalenecarboximidamide $^1$H NMR (300 MHz, DMSO) δ 1.76 (s, 3H), 4.50 (AB quartet, 2H), 4.90 (s, 2H), 7.18–7.30 (m, $^5$H), 7.55 (d, 2H), 7.63 (d, 1H), 7.78–7.83 (m, 3H), 7.95 (d, 1H), 8.05 (d, 1H), 8.13 (d, 1H), 8.23 (s, 1H), 8.43 (s, 1H), 9.18 (s, 2H), 9.40 (s, 2H), 9.72 (s, 1H).

25. 7-[[3-[3-(aminophenyl)methyl]-4-[4-(1H-imidazol-1-yl)phenyl]-4-methyl-2,5-dioxo-1-imidazolidinyl]methyl]-2-naphthalenecarboximidamide $^1$H NMR (300 MHz, DMSO) δ 1.80 (s, 3H), 4.50 (AB quartet, 2H), 4.90 (s, 2H), 7.20–7.40 (m, $^4$H), 7.57 (d, 2H), 7.60 (d, 1H), 7.78–7.85 (m, 3H), 7.95 (d, 2H), 8.05 (d, 1H), 8.15 (d, 1H), 8.23 (s, 1H), 8.44 (s, 1H), 9.22 (s, 2H), 9.42 (s, 2H), 9.68 (s, 1H).

26. 3-[[3-[[7-(aminoiminomethyl)-2-naphthalenyl]methyl]-5-[4-(1H-imidazol-1-yl)phenyl]-5-methyl-2,4-dioxo-1-imidazolidinyl]methyl]benzoic acid methyl ester $^1$H NMR (300 MHz, DMSO) δ 1.80 (s, 3H), 3.75 (s, 3H), 4.55 (AB quartet, 2H), 4.90 (s, 2H), 7.38 (t, 1H), 7.50 (d, 3H), 7.62–7.88 (m, $^6$H), 7.98 (d, 2H), 8.08 (d, 1H), 8.17 (d, 1H), 8.23 (s, 1H), 8.43 (s, 1H), 9.23 (s, 2H), 9.42 (s, 2H), 9.65 (s, 1H).

27. 7-[[3-[(3-aminophenyl)methyl]-4-(1,3-benzodioxol-5-yl)-4-methyl-2,5-dioxo-1-imidazolidinyl]methyl-2-naphthalenecarboximidamide $^1$H NMR (300 MHz, DMSO) δ 1.63 (s, 3H), 4.42 (AB quartet, 2H), 4.88 (s, 2H), 6.00 (s, 2H), 6.70 (m, 2H), 6.87 (d, 1H), 7.20–7.40 (m, $^4$H), 7.60 (d, 1H), 7.80 (d, 1H), 7.90 (s, 1H), 8.05 (d, 1H), 8.15 (d, 1H), 8.40 (s, 1H), 9.20 (s, 2H), 9.40 (s, 2H).

28. 7-[[4-(1,3-benzodioxol-5-yl)-4-methyl-2,5-dioxo-3-(phenylmethyl)-1-imidazolidinyl]methyl]-2-naphthalenecarboximidamide $^1$H NMR (300 MHz, DMSO) δ 1.60 (s, 3H), 4.36 (AB quartet, 2H), 4.84 (s, 2H), 6.00 (s, 2H), 6.70–6.80 (m, 2H), 6.85 (d, 1H), 7.15–7.25 (m, $^5$H), 7.64 (d, 1H), 7.80 (d, 1H), 7.90 (s, 1H), 8.05 (d, 1H), 8.15 (d, 1H), 8.41 (s, 1H), 9.15 (s, 2H), 9.40 (s, 2H).

29. 3-[[3-[[7-(aminoiminomethyl)-2-naphthalenyl]methyl]-5-(1,3-benzodioxol-5-yl)-5-methyl-2,4-dioxo-1-imidazolidinyl]methyl]-benzoic acid $^1$H NMR (300 MHz, DMSO) δ 1.64 (s, 3H), 4.45 (AB quartet, 2H), 4.86 (s, 2H), 5.90–6.00 (m, 2H), 6.65–6.78 (m, 2H), 6.82 (d, 1H), 7.30–7.47 (m, 2H), 7.60–7.82 (m, $^4$H), 7.92 (s, 1H), 8.08 (d, 1H), 8.15 (d, 1H), 8.42 (s, 1H), 9.16 (s, 2H), 9.43 (s, 2H).

30. 2-[4-[1-[[7-(aminoiminomethyl)-2-naphthalenyl]methyl]-4-methyl-2,5-dioxo-3-(phenylmethyl)-4-imidazolidinyl]phenoxy]-acetic acid $^1$H NMR (300 MHz, DMSO) δ 1.60 (s, 3H), 4.38 (AB quartet, 2H), 4.64 (s, 2H), 4.88 (s, 2H), 6.90 (d, 2H), 7.10–7.30 (m, $^7$H), 7.60 (d, 1H), 7.82 (d, 1H), 7.93 (s, 1H), 8.06 (d, 1H), 8.15 (d, 1H), 8.43 (s, 1H), 9.15 (s, 2H), 9.42 (s, 2H).

31. 2-[4-[1-[[7-(aminoiminomethyl)-2-naphthalenyl]methyl]-4-methyl-2,5-dioxo-3-(phenylmethyl)-4-imidazolidinyl]phenoxy]-acetic acid methyl ester $^1$H NMR (300 MHz, DMSO) δ 1.60 (s, 3H), 3.65 (s, 3H), 4.35 (AB quartet, 2H), 4.79 (s, 2H), 4.85 (s, 2H), 6.90 (s, 2H), 7.15–7.30 (m, $^7$H), 7.60 (d, 1H), 7.80 (d, 1H), 7.90 (s, 1H), 8.05 (d, 1H), 8.15 (d, 1H), 8.42 (s, 1H), 9.10 (s, 2H), 9.40 (s, 2H).

32. 1-[[7-(aminoiminomethyl)-2-naphthalenyl]methyl]-2,5-dioxo-4-phenyl-4-imidazolidinepentanoic acid methyl ester $^1$H NMR (300 MHz, DMSO) δ 1.00–1.20 (m, 2H), 1.40–1.55 (m, 2H), 1.90–2.10 (m, 2H), 2.18 (t, 2H), 3.47 (s, 3H), 4.78 (s, 2H), 7.26–7.40 (m, 3H), 7.50–7.60 (m, 3H), 7.79 (d, 1H), 7.85 (s, 1H), 8.00 (d, 1H), 8.10 (d, 1H), 8.39 (s, 1H), 9.10–9.20 (m, 3H), 9.40 (s, 2H).

33. 1-[[7-(aminoiminomethyl)-2-naphthalenyl]methyl]-2,5-dioxo-4-phenyl-4-imidazolidineoctanamide $^1$H NMR (300 MHz, DMSO) δ 1.00–1.20 (m, $^8$H), 1.30–1.42 (m, 2H), 1.90–2.10 (m, $^4$H), 4.78 (s, 2H), 7.25–7.40 (m, 3H), 7.50 (d, 2H), 7.57 (d, 1H), 7.78 (d, 1H), 7.85 (d, 1H), 8.00 (d, 1H), 8.08 (d, 1H), 8.39 (s, 1H), 9.05–9.15 (m, 3H), 9.43 (s, 2H).

34. 1-[[7-(aminoiminomethyl)-2-naphthalenyl]methyl]-2,5-dioxo-4-phenyl-4-imidazolidineoctanoic acid methyl ester $^1$H NMR (300 MHz, DMSO) δ 1.00–1.20 (m, $^8$H), 1.30–1.42 (m, 2H), 1.85–2.10 (m, 2H), 2.18 (t, 2H), 3.55 (s, 3H), 4.78 (s, 2H), 7.25–7.40 (m, 3H), 7.50 (d, 2H), 7.59 (d, 1H), 7.80 (d, 1H), 7.86 (s, 1H), 7.99 (d, 1H), 8.08 (d, 1H), 8.40 (s, 1H), 9.10–9.20 (m, 3H), 9.40 (s, 2H).

35. 7-[[4-methyl-4-[4-[methyl(phenylmethyl)aminophenyl]-2,5-dioxo-3-(phenylmethyl)-1-imidazolidinyl]methyl]-2-naphthalene carboximidamide $^1$H NMR (300 MHz, DMSO) δ 1.58 (s, 3H), 3.00 (s, 3H), 4.25 (AB quartet, 2H), 4.75 (s, 2H), 4.85 (s, 2H), 6.68 (d, 2H), 7.00 (d, 2H), 7.15–7.35 (m, $^{10}$H), 7.60 (d, 1H), 7.80 (d, 1H), 7.90 (s, 1H), 8.03 (d, 1H), 8.15 (d, 1H), 8.40 (s, 1H), 9.04 (s, 2H), 9.43 (s, 2H).

36. 7-[[4-(4-aminophenyl)-4-methyl-2,5-dioxo-3-phenylmethyl-1-imidazolidinyl]methyl]-2-naphthalene carboximidamide $^1$H NMR (300 MHz, DMSO) δ 1.55 (s, 3H), 4.20 (AB quartet, 2H), 4.85 (s, 2H), 6.58 (d, 2H), 6.90 (d, 2H), 7.20–7.30 (m, $^5$H), 7.60 (d, 1H), 7.80 (d, 1H), 7.95 (s, 1H), 8.05 (d, 1H), 8.15 (d, 1H), 8.43 (s, 1H), 9.05 (s, 2H), 9.43 (s, 2H).

37. 1-[[7-(aminoiminomethyl)-2-naphthalenyl]methyl]-2,5-dioxo-4-phenyl-4-imidazolidinepentanoic acid $^1$H NMR (300 MHz, DMSO) δ 1.05–1.20 (m, 2H), 1.40–1.50 (m, 2H), 1.95–2.15 (m, $^4$H), 4.77 (s, 2H), 7.30–7.41 (m, 3H), 7.50–7.60 (m, 3H), 7.79 (d, 1H), 7.84 (s, 1H), 8.00 (d, 1H), 8.10 (d, 1H), 8.38 (s, 1H), 9.08 (s, 2H), 9.18 (s, 1H), 9.40 (s, 2H).

38. 1-[[7-(aminoiminomethyl)-2-naphthalenyl]methyl]-2,5-dioxo-4-phenyl-4-imidazolidinepentanamide $^1$H NMR (300 MHz, DMSO) δ 1.00–1.22 (m, 2H), 1.36–1.58 (m, 2H), 1.90–2.20 (m, $^4$H), 4.76 (s, 2H), 7.30–7.42 (m, 3H), 7.45–7.60 (m, 3H), 7.78 (d, 1H), 7.83 (s, 1H), 8.00 (d, 1H), 8.10 (d, 1H), 8.40 (s, 1H), 9.10 (s, 2H), 9.18 (s, 1H), 9.42 (s, 2H).

39. 1-[[7-(aminoiminomethyl)-2-naphthalenyl]methyl]-2,5-dioxo-4-phenyl-4-imidazolidineoctanoic acid $^1$H NMR (300 MHz, DMSO) δ 0.95–1.25 (m, $^8$H), 1.30–1.42 (m, 2H), 1.85–2.20 (m, $^4$H), 4.78 (s, 2H), 7.30–7.42 (m, 3H), 7.50–7.60 (m, 3H), 7.80 (d, 1H), 7.88 (s, 1H), 8.00 (d, 1H), 8.10 (d, 1H), 8.40 (s, 1H), 9.15 (s, 2H), 9.42 (s, 2H).

40. 7-[[3-[(4-aminophenyl)methyl]-4-methyl-2,5-dioxo-4-phenyl-1-imidazolidinyl]methyl]-2-naphthalenecarboximidamide $^1$H NMR (300 MHz, DMSO) δ 1.63 (s, 3H), 4.36 (AB quartet, 2H), 4.85 (s, 2H), 7.17–7.38 (m, $^9$H), 7.60 (d, 1H), 7.79 (d, 1H), 7.90 (d, 1H), 7.98 (d, 1H), 8.05 (d, 1H), 8.40 (s, 1H), 9.00 (s, 2H), 9.40 (s, 2H).

41. 7-[[3-[(2-aminophenyl)methyl]-4-methyl-2,5-dioxo-4-phenyl-1-imidazolidinyl]methyl]-2-naphthalenecarboximidamide $^1$H NMR (300 MHz, DMSO) δ 1.75 (s, 3H), 4.42 (AB quartet, 2H), 4.88 (s, 2H), 7.18–7.40 (m, $^9$H), 7.60 (d, 1H), 7.80 (d, 1H), 7.90 (s, 1H), 8.05 (d, 1H), 8.10 (d, 1H), 8.40 (s, 1H), 9.10 (s, 2H), 9.40 (s, 2H).

42. 7-[[4-methyl-3-[(2-nitrophenyl)methyl]-2,5-dioxo-4-phenyl-1-imidazolidinyl]methyl]-2-naphthalenecarboximidamide ¹H NMR (300 MHz, DMSO) δ 1.80 (s, 3H), 4.45 (AB quartet, 2H), 4.90 (s, 2H), 7.10 (s, 1H), 7.00–7.20 (m, 8H), 7.60 (d, 1H), 7.80 (d, 1H), 7.92 (s, 1H), 8.02 (d, 1H), 8.10 (d, 1H), 8.40 (s, 1H), 9.05 (s, 2H), 9.40 (s, 2H).

43. 7-[[4-(4-aminophenyl)-4-methyl-2,5-dioxo-1-imidazolidinyl]methyl]-2-naphthalene carboximidamide ¹H NMR (300 MHz, DMSO) δ 1.60 (s, 3H), 4.75 (s, 2H), 6.64 (d, 2H), 7.18 (d, 2H), 7.58 (d, 1H), 7.75 (d, 1H), 7.83 (s, 1H), 8.03 (d, 1H), 8.10 (d, 1H), 8.40 (d, 1H), 8.90 (s, 1H), 9.04 (s, 2H), 9.40 (s, 2H).

44. 7-[[2,5-dioxo-4-phenyl-3,4-bis(phenylmethyl)-1-imidazolidinyl]methyl]-2-naphthalene carboximidamide ¹H NMR (300 MHz, DMSO) δ 3.70 (AB quartet, 2H), 4.50–4.65 (m, 4H), 6.85–7.12 (m, 1H), 7.20–7.35 (m, 5H), 7.72 (s, 1H), 7.80 (d, 1H), 7.85 (d, 1H), 8.10 (d, 1H), 8.26 (s, 1H), 9.00–9.44 (m, 4H).

45. 7-[[2,5-dioxo-4-phenyl-4-(2-phenylethyl)-3-phenylmethyl-1-imidazolidinyl]methyl]-2-naphthalene carboximidamide ¹H NMR (300 MHz, DMSO) δ 1.38 (s, 3H), 1.80–2.08 (m, 4H), 4.55 (AB quartet, 2H), 4.80–4.90 (m, 2H), 6.65 (d, 2H), 7.03–7.16 (m, 3H), 7.24–7.35 (m, 3H), 7.45 (d, 2H), 7.64 (d, 1H), 7.78 (d, 1H), 7.88 (s, 1H), 8.05 (d, 1H), 8.11 (d, 1H), 8.43 (s, 1H), 9.05 (s, 2H), 9.40 (s, 2H).

46. 7-[[4-(4-aminophenyl)-3,4-dimethyl-2,5-dioxo-1-imidazolidinyl]methyl]-2-naphthalene carboximidamide ¹H NMR (300 MHz, DMSO) δ 1.69 (s, 3H), 2.65 (s, 3H), 4.80 (s, 2H), 6.63 (d, 2H), 6.95 (d, 2H), 7.57 (d, 1H), 7.76 (d, 1H), 7.85 (s, 1H), 8.02 (d, 1H), 8.10 (d, 1H), 8.42 (s, 1H), 9.05 (s, 2H), 9.40 (s, 2H).

47. 7-[[4-methyl-4-(4-dimethylaminophenyl)-2,5-dioxo-3-(phenylmethyl)-1-imidazolidinyl]methyl]-2-naphthalene carboximidamide ¹H NMR (300 MHz, DMSO) δ 1.56 (s, 3H), 2.86 (s, 6H), 4.30 (AB quartet, 2H), 4.87 (s, 2H), 6.69 (d, 2H), 7.00 (d, 2H), 7.18–7.30 (m, 5H), 7.63 (d, 1H), 7.68 (d, 1H), 7.84 (s, 1H), 8.05 (d, 1H), 8.12 (d, 1H), 8.40 (s, 1H), 9.08 (s, 2H), 9.40 (s, 2H).

48. 7-[[4-methyl-2,5-dioxo-4-[4-[(phenylmethyl)aminophenyl]-3-(phenylmethyl)-1-imidazolidinyl]methyl]-2-naphthalene carboximidamide ¹H NMR (300 MHz, DMSO) δ 1.50 (s, 3H), 4.21 (s, 2H), 4.24 (AB quartet, 2H), 4.83 (s, 2H), 6.50 (d, 2H), 6.90 (d, 2H), 7.10–7.30 (m, 10H), 7.60 (d, 1H), 7.80 (d, 1H), 7.90 (s, 1H), 8.04 (d, 1H), 8.12 (d, 1H), 8.40 (s, 1H), 9.10 (s, 2H), 9.40 (s, 2H).

49. 7-[[4-(4-aminophenyl)-3-[(3-aminophenyl)methyl]-4-methyl-2,5-dioxo-1-imidazolidinyl]methyl]-2-naphthalene carboximidamide ¹H NMR (300 MHz, DMSO) δ 1.50 (s, 3H), 4.20 (AB quartet, 2H, partially obscured by water), 4.85 (s, 2H), 6.58 (d, 2H), 6.60–6.78 (m, 3H), 6.88 (d, 2H), 7.08 (t, 1H), 7.60 (d, 1H), 7.78 (d, 1H), 7.90 (s, 1H), 8.04 (d, 1H), 8.12 (d, 1H), 8.42 (s, 1H), 9.04 (s, 2H), 9.40 (s, 2H).

50. 3-[[7-(aminoiminomethyl)-2-naphthalenyl]methyl]-5-methyl-2,4-dioxo-5-phenyl-1-imidazolidinebutanoic acid ethyl ester ¹H NMR (300 MHz, DMSO) δ 1.10 (t, 3H), 1.60–1.75 (m, 2H), 1.85 (s, 3H), 2.20 (t, 2H), 2.90–3.00 (m, 1H), 3.25–3.30 (m, 1H), 3.95 (q, 2H), 4.80 (br s, 2H), 7.20–7.50 (m, 5H), 7.55 (d, 1H), 7.75 (d, 1H), 7.85 (s, 1H), 8.05 (d, 1H), 8.10 (d, 1H), 8.40 (s, 1H), 9.05 (s, 2H), 9.40 (s, 2H).

51. 3-[[7-(aminoiminomethyl)-2-naphthalenyl]methyl]-5-methyl-2,4-dioxo-5-phenyl-1-imidazolidinebutanoic acid methyl ester ¹H NMR (300 MHz, DMSO) δ 1.60–1.75 (m, 2H), 1.80 (s, 3H), 2.25 (t, 2H), 2.90–3.00 (m, 1H), 3.25–3.35 (m, 1H), 3.50 (s, 3H), 4.80 (s, 2H), 7.25–7.43 (m, 5H), 7.58 (d, 1H), 7.75 (d, 1H), 7.85 (s, 1H), 8.05 (d, 1H), 8.10 (d, 1H), 8.40 (s, 1H), 9.10 (s, 2H), 9.40 (s, 2H).

52. 3-[[7-(aminoiminomethyl)-2-naphthalenyl]methyl]-5-methyl-2,4-dioxo-5-phenyl-1-imidazolidinepentanoic acid ethyl ester ¹H NMR (300 MHz, DMSO) δ1.10 (t, 3H), 1.30–1.50 (m, 4H), 1.80 (s, 3H), 2.15–2.20 (m, 2H), 2.85–3.00 (m, 1H), 3.20–3.35 (m, 1H), 3.90 (q, 2H), 4.80 (s, 2H), 7.20–7.40 (m, 5H), 7.58 (d, 1H), 7.75 (d, 1H), 7.85 (s, 1H), 8.00 (d, 1H), 8.10 (d, 1H) 8.40 (s, 1H), 9.10 (s, 2H), 9.40 (s, 2H).

53. 3-[[7-(aminoiminomethyl)-2-naphthalenyl]methyl]-5-methyl-2,4-dioxo-5-phenyl-1-imidazolidineacetic acid ¹H NMR (300 MHz, DMSO) δ1.80 (s, 3H), 3.95 (AB quartet, 2H), 4.85 (s, 2H), 7.30–7.42 (m, 5H), 7.58 (d, 1H), 7.75 (d, 1H), 7.90 (s, 1H), 8.03 (d, 1H), 8.10 (d, 1H), 8.40 (s, 1H), 9.05 (s, 2H), 9.42 (s, 2H).

54. 3-[[7-(aminoiminomethyl)-2-naphthalenyl]methyl]-5-methyl-2,4-dioxo-5-phenyl-1-imidazolidineacetamide ¹H NMR (300 MHz, DMSO) δ1.75 (s, 3H), 3.75 (AB quartet, 2H), 4.85 (s, 2H), 7.10 (br s, 1H), 7.25–7.50 (m, 4H), 7.58 (d, 1H), 7.78 (d, 1H), 7.90 (s, 1H), 8.00 (d, 1H), 8.10 (d, 1H), 8.39 (s, 1H), 9.10 (s, 2H), 9.42 (d, 2H).

55. 3-[[7-(aminoiminomethyl)-2-naphthalenyl]methyl]-5-methyl-2,4-dioxo-5-phenyl-1-imidazolidinebutanamide ¹H NMR (300 MHz, DMSO) δ1.60–1.70 (m, 2H), 1.80 (s, 3H), 1.90–2.02 (m, 2H), 2.80–3.00 (m, 1H), 3.25–3.35 (m, 1H), 4.80 (s, 2H), 7.20–7.40 (m, 5H), 7.55 (d, 1H), 7.78 (d, 1H), 7.84 (s, 1H), 8.00 (d, 1H), 8.10 (d, 1H), 8.40 (s, 1H), 9.05 (s, 2H), 9.40 (s, 2H).

56. 3-[[7-(aminoiminomethyl)-2-naphthalenyl]methyl]-5-methyl-2,4-dioxo-5-phenyl-1-imidazolidinepentanoic acid methyl ester ¹H NMR (300 MHz, DMSO) δ1.30–1.50 (m, 4H), 1.80 (s, 3H), 2.20 (t, 2H), 2.85–3.00 (m, 1H), 3.20–3.38 (m, 1H), 3.55 (s, 3H), 4.85 (s, 2H), 7.20–7.43 (m, 5H), 7.60 (d, 1H), 7.78 (d, 1H), 7.90 (s, 1H), 8.05 (d, 1H), 8.15 (d, 1H), 8.40 (s, 1H), 9.05 (s, 2H), 9.43 (s, 2H).

57. 3-[[7-(aminoiminomethyl)-2-naphthalenyl]methyl]-5-methyl-2,4-dioxo-5-phenyl-1-imidazolidinepentamide ¹H NMR (300 MHz, DMSO) δ 1.35–1.45 (m, 4H), 1.80 (s, 3H), 1.95–2.00 (m, 2H), 2.83–2.95 (m, 1H), 3.25–3.40 (m, 1H), 4.80 (s, 2H), 7.30–7.40 (m, 5H), 7.59 (d, 1H), 7.75 (d, 1H), 7.85 (s, 1H), 8.05 (d, 1H), 8.12 (d, 1H), 8.42 (s, 1H), 9.10 (s, 2H), 9.44 (s, 2H).

58. 3-[[7-(aminoiminomethyl)-2-naphthalenyl]methyl]-5-methyl-2,4-dioxo-5-phenyl-1-imidazolidinebutanoic acid ¹H NMR (300 MHz, DMSO) δ1.55–1.65 (m, 2H), 1.80 (s, 3H), 2.10–2.20 (t, 2H), 2.85–3.00 (m, 1H), 3.25–3.40 (m, 1H), 4.80 (s, 2H), 7.20–7.40 (m, 5H), 7.60 (d, 1H), 7.75 (d, 1H), 7.90 (s, 1H), 8.03 (d, 1H), 8.10 (d, 1H), 8.40 (s, 1H), 9.10 (s, 2H), 9.40 (s, 2H).

59. 3-[[7-(aminoiminomethyl)-2-naphthalenyl]methyl]-5-methyl-2,4-dioxo-5-phenyl-1-imidazolidinepentanoic acid, 4-hydroxybutyl ester ¹H NMR (300 MHz, DMSO) δ1.30–1.42 (m, 4H), 1.60–1.78 (m, 4H), 1.80 (s, 3H), 2.15–2.20 (m, 2H), 2.85–3.00 (m, 1H), 3.20–3.35 (m, 1H), 3.60 (t, 2H), 3.95 (t, 2H), 4.80 (s, 2H), 7.23–7.40 (m, 5H), 7.55 (d, 1H), 7.78 (d, 1H), 7.85 (s, 1H), 8.03 (d, 1H), 8.10 (d, 1H), 8.40 (s, 1H), 9.10 (s, 2H), 9.40 (s, 2H).

60. 3-[[7-(aminoiminomethyl)-2-naphthalenyl]methyl]-5-methyl-2,4-dioxo-5-phenyl-1-imidazolidinehexanoic acid ethyl ester ¹H NMR (300 MHz, DMSO) δ1.10–1.20 (m, 5H), 1.30–1.45 (m, 4H), 1.80 (s, 3H), 2.15 (t, 2H), 2.85–2.98 (m, 1H), 3.20–3.35 (m, 1H), 3.95 (q, 2H), 4.80 (s, 2H), 7.20–7.40 (m, 5H), 7.58 (d, 1H), 7.75 (d, 1H), 7.85 (s, 1H), 8.03 (d, 1H), 8.10 (d, 1H), 8.40 (s, 1H), 9.10 (s, 2H), 9.40 (s, 2H).

61. 3-[[7-(aminoiminomethyl)-2-naphthalenyl]methyl]-5-methyl-2,4-dioxo-5-phenyl-1-imidazolidineheptanoic acid ethyl ester $^1$H NMR (300 MHz, DMSO) δ1.05–1.20 (m, 7H), 1.30–1.45 (m, 4H), 1.80 (s, 3H), 2.20 (t, 2H), 2.85–3.00 (m, 1H), 3.20–3.35 (m, 1H), 4.00 (q, 2H), 4.80 (s, 2H), 7.20–7.40 (m, 5H), 7.60 (d, 1H), 7.78 (d, 1H), 7.90 (s, 1H), 8.03 (d, 1H), 8.10 (d, 1H), 8.40 (s, 1H), 9.05 (s, 2H), 9.40 (s, 2H).

62. 3-[[7-(aminoiminomethyl)-2-naphthalenyl]methyl]-5-methyl-2,4-dioxo-5-phenyl-1-imidazolidinehexanoic acid $^1$H NMR (300 MHz, DMSO) δ1.05–1.20 (m, 2H), 1.30–1.40 (m, 4H), 1.80 (s, 3H), 2.10 (t, 2H), 2.85–3.00 (m, 1H), 3.20–3.35 (m, 1H), 4.80 (s, 2H), 7.05–7.23 (m, 5H), 7.60 (d, 1H), 7.78 (d, 1H), 7.90 (s, 1H), 8.03 (d, 1H), 8.15 (d, 1H), 8.40 (s, 1H), 9.10 (s, 2H), 9.40 (s, 2H).

63. 3-[[7-(aminoiminomethyl)-2-naphthalenyl]methyl]-5-methyl-2,4-dioxo-5-phenyl-1-imidazolidineheptanoic acid $^1$H NMR (300 MHz, DMSO) δ1.00–1.20 (m, 4H), 1.23–1.40 (m, 4H), 1.80 (s, 3H), 2.05 (t, 2H), 2.85–3.00 (m, 1H), 3.20–3.30 (m, 1H), 4.80 (s, 2H), 7.25–7.40 (m, 5H), 7.60 d, 1H), 7.78 (d, 1H), 7.90 (s, 1H), 8.04 (d, 1H), 8.10 (d, 1H), 8.40 (s, 1H), 9.10 (s, 2H), 9.40 (s, 2H).

64. 3-[[7-(aminoiminomethyl)-2-naphthalenyl]methyl]-5-methyl-2,4-dioxo-5-phenyl-1-imidazolidinepentanoic acid $^1$H NMR (300 MHz, DMSO) δ1.30–1.45 (m, 4H), 1.80 (s, 3H), 2.00–2.15 (m, 2H), 2.83–3.00 (m, 1H), 3.23–3.35 (m, 1H), 4.80 (s, 2H), 7.23–7.40 (m, 5H), 7.58 (d, 1H), 7.77 (d, 1H), 7.85 (s, 1H), 8.03 (d, 1H), 8.10 (d, 1H), 8.40 (s, 1H), 9.05 (s, 2H), 9.38 (s, 2H).

65. 3-[[7-(aminoiminomethyl)-2-naphthalenyl]methyl]-5-methyl-2,4-dioxo-5-phenyl-1-imidazolidinehexanamide $^1$H NMR (300 MHz, DMSO) δ 1.13–1.20 (m, 2H), 1.30–1.42 (m, 4H), 1.80 (s, 3H), 1.95 (t, 2H), 2.83–2.95 (m, 1H), 3.20–3.30 (m, 1H), 4.80 (s, 2H), 7.05–7.20 (m, 5H), 7.58 (d, 1H), 7.78 (d, 1H), 7.85 (s, 1H), 8.03 (d, 1H), 8.10 (d, 1H), 8.40 (s, 1H), 9.10 (s, 2H), 9.40 (s, 2H).

66. 3-[[7-(aminoiminomethyl)-2-naphthalenyl]methyl]-5-methyl-2,4-dioxo-5-phenyl-1-imidazolidineheptanamide $^1$H NMR (300 MHz, DMSO) δ 1.05–1.18 (m, 4H), 1.30–1.43 (m, 4H), 1.80 (s, 3H), 1.95 (t, 2H), 2.85–3.00 (m, 1H), 3.20–3.35 (m, 1H), 4.80 (s, 2H), 7.25–7.40 (m, 5H), 7.60 (d, 1H), 7.78 (d, 1H), 7.85 (s, 1H), 8.05 (d, 1H), 8.15 (d, 1H), 8.40 (s, 1H), 9.10 (s, 2H), 9.40 (s, 2H).

67. 4-[1-[[7-(aminoiminomethyl)-2-naphthalenyl]methyl]-4-methyl-2,5-dioxo-3-(phenylmethyl)-4-imidazolidinyl]-benzoic acid $^1$H NMR (300 MHz, DMSO) δ 1.70 (t, 3H), 4.40 (AB quartet, 2H), 4.85 (s, 2H), 7.10–7.25 (m, 5H), 7.38 (d, 2H), 7.60 (d, 1H), 7.80 (d, 1H), 7.88 (s, 1H), 7.90 (d, 2H), 8.05 (d, 1H), 8.16 (d, 1H), 8.40 (s, 1H), 9.05 (s, 2H), 9.42 (s, 2H).

68. 3-[1-[[7-(aminoiminomethyl)-2-naphthalenyl]methyl]-4-methyl-2,5-dioxo-3-(phenylmethyl)-4-imidazolidinyl]-benzoic acid $^1$H NMR (300 MHz, DMSO) δ 1.75 (s, 3H), 4.40 (AB quartet, 2H), 4.90 (s, 2H), 7.10–7.20 (m, 5H), 7.40–7.55 (m, 2H), 7.60 (d, 1H), 7.75–7.92 (m, 4H), 8.05 (d, 1H), 8.13 (d, 1H), 8.40 (s, 1H), 9.03 (s, 2H), 9.40 (s, 2H).

69. 4-[1-[[7-(aminoiminomethyl)-2-naphthalenyl]methyl]-4-methyl-2,5-dioxo-3-(phenylmethyl)-4-imidazolidinyl]-benzamide $^1$H NMR (300 MHz, DMSO) δ 1.70 (s, 3H), 4.40 (AB quartet, 2H), 4.90 (s, 2H), 7.15–7.25 (m, 5H), 7.30 (d, 2H), 7.38–7.42 (m, 1H), 7.60 (d, 1H), 7.80–8.00 (m, 3H), 8.05 (d, 1H), 8.12 (d, 1H), 8.43 (s, 1H), 9.20 (s, 2H), 9.43 (s, 2H).

70. 1-[[7-(aminoiminomethyl)-2-naphthalenyl]methyl]-2,5-dioxo-3-(phenylmethyl)-4-imidazolidineacetic acid $^1$H NMR (300 MHz, DMSO) δ 2.80 (s, 2H), 4.25–4.30 (m, 1H), 4.54 (AB quartet, 2H), 4.82 (AB quartet, 2H), 7.22–7.50 (m, 5H), 770 (d, 1H), 7.80 (d, 1H), 8.00–8.10 (m, 2H), 8.18 (d, 1H), 8.42 (s, 1H), 9.20 (s, 2H), 9.46 (d, 2H).

71. 3-[1-[[7-(aminoiminomethyl)-2-naphthalenyl]methyl]-4-methyl-2,5-dioxo-3-(phenylmethyl)-4-imidazolidinyl]-benzamide $^1$H NMR (300 MHz, DMSO) δ 1.75 (s, 3H), 4.40 (AB quartet, 2H), 4.90 (s, 2H), 7.10–7.23 (m, 5H), 7.40–7.55 (m, 2H), 7.62 (d, 1H), 7.75–7.90 (m, 4H), 8.03–8.18 (m, 2H), 8.45 (s, 1H), 9.00 (s, 2H), 9.40 (s, 2H).

72. 4-[1-[[7-(aminoiminomethyl)-2-naphthalenyl]methyl]-4-methyl-2,5-dioxo-3-(phenylmethyl)-4-imidazolidinyl]-benzoic acid methyl ester $^1$H NMR (300 MHz, DMSO) δ 1.75 (s, 3H), 3.80 (s, 3H), 4.40 (AB quartet, 2H), 4.90 (s, 2H), 7.15–7.23 (m, 5H), 7.40 (d, 2H), 7.60 (d, 1H), 7.78 (d, 1H), 7.90–7.95 (m, 3H), 8.05 (d, 1H), 8.15 (d, 1H), 8.40 (s, 1H), 9.05 (s, 2H), 9.42 (s, 2H).

73. 4-[1-[[7-(aminoiminomethyl)-2-naphthalenyl]methyl]-2,5-dioxo-4-phenyl-4-imidazolidinyl]-benzoic acid methyl ester $^1$H NMR (300 MHz, DMSO) δ 3.80 (s, 3H), 4.85 (s, 2H), 7.25–7.40 (m, 5H), 7.50 (d, 2H), 7.58 (d, 1H), 7.78 (d, 1H), 7.85 (s, 1H), 7.97–8.05 (m, 3H), 8.10 (d, 1H), 8.35 (s, 1H), 9.08 (s, 2H), 9.40 (s, 2H), 9.90 (s, 1H).

74. 3-[1-[[7-(aminoiminomethyl)-2-naphthalenyl]methyl]-2,5-dioxo-4-phenyl-4-imidazolidinyl]-benzoic acid $^1$H NMR (300 MHz, DMSO) δ 4.85 (s, 2H), 7.25–7.43 (m, 5H), 7.50–7.60 (m, 3H), 7.58 (d, 1H), 7.80–7.96 (m, 2H), 7.96–8.05 (m, 2H), 8.10 (d, 1H), 8.35 (s, 1H), 9.00 (s, 2H), 9.40 (s, 2H), 9.90 (s, 1H).

75. 1-[[7-(aminoiminomethyl)-2-naphthalenyl]methyl]-2,5-dioxo-4-phenyl-3-(phenylmethyl)-4-imidazolidineacetic acid $^1$H NMR (300 MHz, DMSO) δ 3.38 (AB quartet, 2H), 4.40 (AB quartet, 2H), 4.85 (s, 2H), 7.15–7.20 (m, 5H), 7.23–7.38 (m, 5H), 7.65 (d, 1H), 7.78 (d, 1H), 7.95–8.03 (m, 2H), 8.15 (d, 1H), 8.38 (s, 1H), 9.10 (s, 2H), 9.40 (s, 2H).

76. 1-[[7-(aminoiminomethyl)-2-naphthalenyl]methyl]-2,5-dioxo-4-phenyl-3-(phenylmethyl)-4-imidazolidinepropanamide $^1$H NMR (300 MHz, DMSO) δ 1.65–1.85 (m, 2H), 2.35–2.45 (m, 2H), 4.38 (AB quartet, 2H), 4.90 (s, 2H), 7.05–7.30 (m, 10H), 7.63 (d, 1H), 7.80 (d, 1H), 7.97 (s, 1H), 8.04 (d, 1H), 8.15 (d, 1H), 8.40 (s, 1H), 9.10 (s, 2H), 9.40 (s, 2H).

77. 4-[1-[[7-(aminoiminomethyl)-2-naphthalenyl]methyl]-2,5-dioxo-4-phenyl-4-imidazolidinyl]-benzamide $^1$H NMR (300 MHz, DMSO) δ 4.85 (s, 2H), 7.30–7.43 (m, 7H), 7.58 (d, 1H), 7.78 (d, 1H), 7.88 (d, 2H), 7.96 (s, 1H), 8.03 (d, 1H), 8.12 (d, 1H), 8.38 (s, 1H), 9.00 (s, 2H), 9.40 (s, 2H) 9.85 (s, 1H).

78. 4-[1-[[7-(aminoiminomethyl)-2-naphthalenyl]methyl]-2,5-dioxo-4-phenyl-4-imidazolidinyl]-benzoic acid $^1$H NMR (300 MHz, DMSO) δ 4.85 (s, 2H), 5.75 (s, 1H), 7.30–7.40 (m, 5H), 7.48 (d, 2H), 7.58 (d, 1H), 7.78 (d, 1H). 7.88 (s, 1H), 7.95 (d, 2H), 8.03 (d, 1H), 8.10 (d, 1H), 8.37 (s, 1H), 9.00 (s, 2H), 9.40 (s, 2H), 9.90 (s, 1H).

79. 3-[1-[[7-(aminoiminomethyl)-2-naphthalenyl]methyl]-2,5-dioxo-4-phenyl-4-imidazolidinyl]-benzamide ¹H NMR (300 MHz, DMSO) δ 4.85 (s, 2H), 7.30–7.55 (m, ⁶H), 7.60 (d, 1H), 7.78 (d, 1H), 7.83–7.90 (m, 2H), 7.96 (s, 1H), 8.00–8.10 (m, 2H), 8.15 (d, 1H), 8.40 (s, 1H), 9.00 (s, 2H), 9.40 (s, 2H), 9.83 (s, 1H).

80. 1-[[7-(aminoiminomethyl)-2-naphthalenyl]methyl]-2,5-dioxo-4-phenyl-3-(phenylmethyl)-4-imidazolidineacetic acid methyl ester
¹H NMR (300 MHz, DMSO) δ 3.20 (s, 3H), 3.40 (AB quartet, 2H), 4.50 (AB quartet, 2H), 4.85 (s, 2H), 7.12–7.43 (m, ¹⁰H), 7.63 (d, 1H), 7.78 (d, 1H), 7.98 (s, 1H), 8.02 (d, 1H), 8.10 (d, 1H), 8.38 (s, 1H), 9.08 (s, 2H), 9.40 (s, 2H).

81. 3-[1-[[7-(aminoiminomethyl)-2-naphthalenyl]methyl]-2,5-dioxo-4-phenyl-4-imidazolidinyl]-benzoic acid methyl ester
¹H NMR (300 MHz, DMSO) δ 3.78–3.85 (m, 3H), 4.83 (s, 2H), 7.25–7.40 (m, ⁵H), 7.55–7.65 (m, 3H), 7.78 (d, 1H), 7.85 (s, 1H), 7.95 (d, 1H), 8.00–8.08 (m, 2H), 8.10 (d, 1H), 8.35 (s, 1H), 9.05 (s, 2H), 9.38 (s, 2H), 9.95 (s, 1H).

82. 1-[[7-(aminoiminomethyl)-2-naphthalenyl]methyl]-2,5-dioxo-4-phenyl-3-(phenylmethyl)-4-imidazolidinepropanoic acid methyl ester
¹H NMR (300 MHz, DMSO) δ 1.80–1.90 (m, 2H), 2.30–2.60 (m, 2H, partially obscured by DMSO, 3.40 (s, 3H), 4.25 (AB quartet, 2H), 4.86 (s, 2H), 7.10–7.40 (m, ¹⁰H), 7.60 (d, 1H), 7.79 (d, 1H), 7.95 (s, 1H), 8.05 (d, 1H), 8.15 (d, 1H), 8.40 (s, 1H), 9.10 (s, 2H), 9.40 (s, 2H).

83. 1-[[7-(aminoiminomethyl)-2-naphthalenyl]methyl]-2,5-dioxo-4-phenyl-3-(phenylmethyl)-4-imidazolidineacetamide
¹H NMR (300 MHz, DMSO) δ 3.30 (AB quartet, 2H, partially obscured by water), 4.35 (AB quartet, 2H), 4.79–4.90 (m, 2H), 6.90 (s, 1H), 7.05–7.35 (m, ⁹H), 7.65 (d, 1H), 7.78 (d, 1H), 8.00–8.05 (m, 2H), 8.12 (d, 1H), 8.38 (s, 1H), 9.00 (s, 2H), 9.40 (s, 2H), 84. 1-[[7-(aminoiminomethyl)-2-naphthalenyl]methyl]-2,5-dioxo-4-phenyl-3-(phenylmethyl)-4-imidazolidinepropanoic acid
¹H NMR (300 MHz, DMSO) δ 1.76 (t, 2H), 2.35–2.40 (m, 2H, partially obscured by DMSO), 4.30 (AB quartet, 2H), 4.90 (s, 2H), 7.10–7.38 (m, ¹⁰H), 7.62 (d, 1H), 7.80 (d, 1H), 7.98 (s, 1H), 8.03 (d, 1H), 8.12 (d, 1H), 8.40 (s, 1H), 9.10 (s, 2H), 9.40 (s, 2H), 85. 7-[[4-methyl-4-(2-naphthalenyl)-2,5-dioxo-3-(phenylmethyl)-1-imidazolidinyl]methyl]-2-naphthalene carboximidamide
¹H NMR (300 MHz, DMSO) δ 1.80 (s, 3H), 4.40 (AB quartet, 2H), 3.90 (s, 2H), 7.15–7.25 (m, ⁶H), 7.50–7.58 (m, 2H), 7.63 (d, 1H), 7.78 (d, 1H), 7.88–7.98 (m, ⁵H), 8.08 (d, 1H), 8.15 (d, 1H), 8.38 (s, 1H), 9.05 (s, 2H), 9.40 (s, 2H).

86. 7-[[4-methyl-4-(2-naphthalenyl)-2,5-dioxo-1-imidazolidinyl]methyl]-2-naphthalene carboximidamide
¹H NMR (300 MHz, DMSO) δ 1.83 (s, 3H), 4.80 (s, 2H), 7.50–7.60 (m, ⁴H), 7.78 (d, 1H), 7.85 (s, 1H), 7.88–7.95 (m, 3H), 8.00–8.05 (m, 2H), 8.10 (d, 1H), 8.38 (s, 1H), 9.00 (s, 2H), 9.20 (s, 1H), 9.39 (s, 2H).

87. 7-[[2,5-dioxo-3,4,4-tris(phenylmethyl)-1-imidazolidinyl]methyl]-2-naphthalene carboximidamide
¹H NMR (300 MHz, DMSO) δ 3.23 (AB quartet, ⁴H, partially obscured by H₂O), 4.38 (s, 2H), 4.70 (s, 2H), 6.75–6.83 (m, ⁵H), 6.95–7.10 (m, ⁶H), 7.28–7.38 (m, 3H), 7.42–7.50 (m, 2H), 7.55 (s, 1H), 7.79 (t, 2H), 8.10 (d, 1H), 8.13 (s, 1H), 9.05 (s, 2H), 9.40 (s, 2H).

88. 7-[[2,5-dioxo-4-phenyl-4-(phenylmethyl)-1-imidazolidinyl]methyl]-2-naphthalene carboximidamide
¹H NMR (300 MHz, DMSO) δ 3.30 (AB quartet, ⁴H, partially obscured by H₂O), 4.45 (AB quartet, 2H), 7.03 (d, 1H), 7.08–7.20 (m, ⁵H), 7.35–7.50 (m, 3H), 7.60 (s, 1H), 7.69 (d, 2H), 7.78 (d, 1H), 7.83 (d, 1H), 8.10 (d, 1H), 8.30 (s, 1H), 9.08 (s, 2H), 9.20 (s, 1H), 9.40 (s, 2H).

89. 7-[[2,5-dioxo-4,4-bis(phenylmethyl)-1-imidazolidinyl]methyl]-2-naphthalene carboximidamide
¹H NMR (300 MHz, DMSO) δ 3.03 (AB quartet, ⁴H), 4.18 (s, 2H), 6.85 (d, 1H), 7.10–7.20 (m, ¹⁰H), 7.32 (s, 1H), 7.70–7.80 (m, 2H), 8.05 (d, 1H), 8.20 (s, 1H), 8.55 (s, 1H), 9.00 (s, 2H), 9.40 (s, 2H).

90. 7-[[4-(2-methylpropyl)-2,5-dioxo-1-imidazolidinyl]methyl]-2-naphthalene carboximidamide
¹H NMR (300 MHz, DMSO) δ 0.80–0.90 (m, ⁶H), 1.38–1.60 (m, 2H), 1.70–1.82 (m, 1H), 4.75 (m, 1H), 4.75 (s, 2H), 7.60 (d, 1H), 7.78 (d, 1H), 7.90 (s, 1H), 8.00 (d, 1H), 8.05 (d, 1H), 8.40–8.45 (m, 2H), 9.05 (s, 2H), 9.40 (s, 2H).

Example 3

The compounds made according to the invention were tested for inhibition of Factor VIIa/TF and as anti-coagulants as follows:

Primary Bioassay of Human Factor VIIa, Human TF, S-2266 Chromogenic Substrate

Assay Principle:

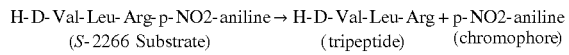

H-D-Val-Leu-Arg-p-NO2-aniline → H-D-Val-Leu-Arg + p-NO2-aniline
(S-2266 Substrate)      (tripeptide)      (chromophore)

The tripeptide p-nitroanilide amide bond of the S-2266 substrate is hydrolyzed by the factor VIIa protease. The liberated, chromophoric cleavage product, p-nitroaniline, is monitored at 405 nm and the concentration of product formed per unit time is calculated using a molar extinction coefficient of 9920 M-1.cm-1 (pathlength=0.6 cm for 200 uL).

Materials and Equipment:
1. Vmax microplate reader (Molecular Devices Corporation).
2. 96-well, flat-bottom microtiter plate (Dynatech Laboratories).
3. 8-channel and 12-channel digital micro pipettes (Oxford Labware).
4. Gilson pipetman P-20, P-100, P-250, P-1000.
5. Sterile pipette tips.
6. Reservoir trays (Costar).
7. Borosilicate glass culture tubes (13×100 mm).

Assay Reagents and Solutions:
1. Assay Buffer: 50 mM Tris HCl, 0.15 M NaCl, 5.0 mM CaCl₂, 0.1% polyethylene glycol (6K), 0.02% NaN₃, pH 7.50.
2. Human factor VIIa (Haematologic Technologies, Inc.):
   Stock solution: listed FVIIa concentration in 50% glycerol.
   Working solution (4×): 40 nM. Prepare fresh.
3. Human rec-Tissue Factor, non-lipidated (TF, American Diagnostica):
   Stock solution: 833 nM (25 ug reconstituted with 1.0 ml sterile Q-H2O), stored at 20 C or colder.
   Working solution (4×): 60 nM. Prepare fresh.
4. S-2266 chromogenic substrate (Kabi Pharmacia Hepar, Inc.):
   Working solution (4×)(if using non-lipidated human rec-TF): 3.2 mM in assay buffer, stored at −2–8° C.

Working solution(4×)(if using soluble TF): 4 mM in assay buffer, store at 2–8° C.
5. Test compounds:
   Stock solution: 10 mM in DMSO
   Working solution(4×): 40 uM.

Assay Procedure:

Assays were performed in 96-well microtiter plates in a total volume of 200 uL containing in final concentration of 50 mM Tris.HCl, 0.15 M NaCl, 5.0 mM $CaCl_2$, 0.1% polyethylene glycol (6K), 0.02% $NaN_3$, pH 7.50 (adjusted at 20° C.) and 10 nM FVIIa, 15 nM TF and 0.8 mM (Km) S-2266 at room temperature (typically 20° C.).

1. Each Pool 10 plate is diluted 1:2 in $dH_2O$. (i.e., 10 ul of 1 mM stock compound in 100% DMSO) is diluted with 10 ul of $H_2O$ to make a 500 uM concentration).
2. Add 4 uls of diluted compounds(500 uM) to 46 uls of assay buffer in a 96 well microtiter plate to make a 1:25 dilution (40 uM—4× working solution).
3. Add 50 uls of controls (assay buffer+4% DMSO) to wells A12–D12 and 50 uls of standard compound 7-[[3-[[4-(aminoiminomethyl)phenyl]methyl]-2,3-dihydro-2-oxo-4,5-diphenyl-1H-imidizol-1-yl]methyl]-2-naphthylene (1.6 uM) to wells E12–H12.
4. Add 100 uls of tissue factor/VIIa complex to all wells.
5. Add 50 uls of substrate (S2266) to all wells.
6. Measure the enzymatic activity at 405 nm. for 2 minutes with 10 second-read interval in Molecular Devices Thermomax plate reader using the one-time automix option.

Calculation of the Ki of Test Compounds:

The S-2266 enzyme-hydrolysis rate is determined in units of mO.D./minute using a range of optical-density reading that best reflect initial-velocity conditions (the earlier time readings usually best, longer time range if enzymatic activity is limiting).

IC50 of the test compounds is derived from the four-parameter, curve-fit program (Molecular Devices). The competitive-inhibition constant (Ki) is calculated from the IC50 value using the equation:

$$Ki=IC50/(1+([S]/Km))$$

Because [S]=Km: Ki=IC50/2

Each compound listed in Example 2 above was tested according to the above-described bioassay. Each compound listed in Example 2 was found to inhibit Factor VIIa/TF activity. Specifically, the compounds described in Example 2 have Ki values of about 5 uM or less, indicating their utility as anticoagulants and antithrombotic agents. In addition, the compounds listed in Example 2 were tested according to bioassays well known to those skilled in the art, such as described in U.S. Pat. No. 5,849,759, and have shown activity for inhibition of other enzymes in the coagulation cascade, such as Factor Xa and thrombin.

Example 4

Preparation of Representative Pharmaceutical Compositions for Oral Administration This example illustrates the preparation of representative pharmaceutical compositions for oral administration containing a compound of the present invention, or a pharmaceutically acceptable salt thereof, e.g., 1-[[7-(aminoiminomethyl)-2-naphthalenyl]methyl]-2,5-dioxo-4-phenyl-3-(phenylmethyl)-4-imidazolidineacetamide.

| 1. Ingredients | % wt./wt. |
|---|---|
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| 2. Ingredients | % wt./wt. |
|---|---|
| Compound of the invention | 20.0% |
| Magnesium stearate | 0.9% |
| Starch | 8.6% |
| Lactose | 69.6% |
| PVP (polyvinylpyrrolidine) | 0.9% |

The above ingredients, with the exception of the magnesium stearate, are combined and granulated using water as a granulating liquid. The formulation is then dried, mixed with the magnesium stearate and formed into tablets with an appropriate tableting machine.

| 3. Ingredients | % wt./wt. |
|---|---|
| Compound of the invention | 0.1 g |
| Propylene glycol | 20.0 g |
| Polyethylene glycol 400 | 20.0 g |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution, which is filtered and bottled.

| 4. Ingredients | % wt./wt. |
|---|---|
| Compound of the invention | 20.0% |
| Peanut oil | 78.0% |
| Span 60 | 2.0% |

The above ingredients are melted, mixed and filled into soft elastic capsules.

| 5. Ingredients | % wt./wt. |
|---|---|
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

Example 5

Preparation of Representative Pharmaceutical Compositions for Parenteral Administration This example illustrates the preparation of a representative pharmaceutical formulation for parenteral administration containing a compound of the invention, or a pharmaceutically acceptable salt thereof, e.g., 7-[[4-(4-aminophenyl)-3-[(3-aminophenyl)methyl]-4-methyl-2,5-dioxo-1-imidazolidinyl]methyl]-2-naphthalene carboximidamide.

| Ingredients | % wt./wt. |
| --- | --- |
| Compound of the invention | 0.02 g |
| Propylene glycol | 20.0 g |
| Polyethylene glycol 400 | 20.0 g |
| Polysorbate 80 | 1.0 g |
| 0.9% saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2µ membrane filter and packaged under sterile conditions.

Example 6

Preparation of Representative Pharmaceutical Compositions in Suppository Form This example illustrates the preparation of a representative pharmaceutical composition in suppository form containing a compound of the invention, or a pharmaceutically acceptable salt thereof, e.g., 7-[[4-(4-aminophenyl)-3-[(3-aminophenyl)methyl]-4-methyl-2,5-dioxo-1-imidazolidinyl]methyl]-2-naphthalene carboximidamide.

| Ingredients | % wt./wt. |
| --- | --- |
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 7

Preparation of Representative Pharmaceutical Compositions for Insufflation

This example illustrates the preparation of a representative pharmaceutical formulation for insufflation containing a compound of the invention, or a pharmaceutically acceptable salt thereof, e.g., 7-[[4-(4-aminophenyl)-3-[(3-aminophenyl)methyl]-4-methyl-2,5-dioxo-1-imidazolidinyl]methyl]-2-naphthalene carboximidamide.

| Ingredients | % wt./wt. |
| --- | --- |
| Micronized compound of the invention | 1.0% |
| Micronized lactose | 99.0% |

The ingredients are milled, mixed, and packaged in an insufflator equipped with a dosing pump.

Example 8

Preparation of Representative Pharmaceutical Compositions in Nebulized Form

This example illustrates the preparation of a representative pharmaceutical formulation in nebulized form containing a compound of the invention, or a pharmaceutically acceptable salt thereof, e.g., 7-[[4-(4-aminophenyl)-3-[(3-aminophenyl)methyl]-4-methyl-2,5-dioxo-1-imidazolidinyl]methyl]-2-naphthalene carboximidamide.

| Ingredients | % wt./wt. |
| --- | --- |
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

Example 9

Preparation of Representative Pharmaceutical Compositions in Aerosol Form

This example illustrates the preparation of a representative pharmaceutical formulation in aerosol form containing a compound of the invention, or a pharmaceutically acceptable salt thereof, e.g., 7-[[4-(4-aminophenyl)-3-[(3-aminophenyl)methyl]-4-methyl-2,5-dioxo-1-imidazolidinyl]methyl]-2-naphthalene carboximidamide.

| Ingredients | % wt./wt. |
| --- | --- |
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

While the present invention has been described with reference to the specific embodiments thereof, it should be understood by those skilled in the art that various changes and modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims as appended hereto.

The compositions of the invention are useful as effective therapeutic agents and as orally active anticoagulants directed toward thrombotic diseases. These compositions may be used as effective treatment in prevention of ischemic/thrombotic complications following angioplasty. The compositions of the invention may also be used for maintenance of bypass graft patency, treatment/prevention of unstable angina, and prevention of ischemic/thrombotic complications following vascular surgery. Further, the anticoagulant compositions of the invention provide safe and effective treatment for thrombotic complications associated with acute promyelocytic leukemia, diabetes, multiple myeloma, disseminated intravascular coagulation associated with septic shock or complications of pregnancies, purpura fulminans associated with infections, adult respiratory distress syndrome, and thrombotic complications associated with aortic valve or vascular prosthesis.

What is claimed is:

1. A compound, or a pharmaceutically acceptable salt thereof, wherein the compound is selected from the group consisting of:
    1-[[7-(aminoiminomethyl)-2-naphthalenyl]methyl]-2,5-dioxo-4-phenyl-3-(phenylmethyl)-4-imidazolidineacetamide;
    1-[[7-(aminoiminomethyl)-2-naphthalenyl]methyl]-2,5-dioxo-4-phenyl-3-(phenylmethyl)-4-imidazolidineacetic acid;
    1-[[7-(aminoiminomethyl)-2-naphthalenyl]methyl]-2,5-dioxo-4-phenyl-3-(phenylmethyl)-4-imidazolidinepropanamide;
    7-[[4-(4-aminophenyl)-4-methyl-2,5-dioxo-3-(phenylmethyl)-1-imidazolidinyl]methyl]-2-naphthalenecarboximidamide;
    7-[[3-(4-aminophenyl)methyl)-4-methyl-2,5-dioxo-4-phenyl-1-imidazolidinyl]methyl]-2-naphthalenecarboximidamide;
    7-[[4-(4-aminophenyl)-4-methyl-2,5-dioxo-3-(phenylmethyl)-1-imidazolidinyl]methyl]-2-naphthalenecarboximidamide;
    4-[[3-[[7-(aminoiminomethyl)-2-naphthalenyl]methyl]-5-methyl-2,4-dioxo-5-phenyl-1-imidazolidinyl]methyl]-benzamide;
    3-[[3-[[7-(aminoiminomethyl)-2-naphthalenyl]methyl]-5-methyl-2,4-dioxo-5-phenyl-1-imidazolidinyl]methyl]-benzamide;
    7-[[3-[(3-aminophenyl)methyl]-4-methyl-2,5-dioxo-4-phenyl-1-imidazolidinyl]methyl]-2-naphthalenecarboximidamide; and
    7-[[3-[[4-(aminoiminomethyl)phenyl]methyl]-4-methyl-2,5-dioxo-4-phenyl-1-imidazolidinyl]methyl]-2-naphthalene carboximidamide;

as a single stereoisomer, a mixture of individual stereoisomers, or a racemic mixture.

2. A pharmaceutical composition, which composition comprises a pharmaceutically acceptable excipient and a therapeutically effective amount of a compound, or a pharmaceutically acceptable salt thereof, wherein the compound is selected from the group consisting of:
    1-[[7-(aminoiminomethyl)-2-naphthalenyl]methyl]-2,5-dioxo-4-phenyl-3-(phenylmethyl)-4-imidazolidineacetamide;
    1-[[7-(aminoiminomethyl)-2-naphthalenyl]methyl]-2,5-dioxo-4-phenyl-3-(phenylmethyl)-4-imidazolidineacetic acid;
    1-[[7-(aminoiminomethyl)-2-naphthalenyl]methyl]-2,5-dioxo-4-phenyl-3-(phenylmethyl)-4-imidazolidinepropanamide;
    7-[[4-(4-aminophenyl)-4-methyl-2,5-dioxo-3-(phenylmethyl)-1-imidazolidinyl]methyl]-2-naphthalenecarboximidamide;
    7-[[3-(4-aminophenyl)methyl)-4-methyl-2,5-dioxo-4-phenyl-1-imidazolidinyl]methyl]-2-naphthalenecarboximidamide;
    7-[[4-(4-aminophenyl)-4-methyl-2,5-dioxo-3-(phenylmethyl)-1-imidazolidinyl]methyl]-2-naphthalenecarboximidamide;
    4-[[3-[[7-(aminoiminomethyl)-2-naphthalenyl]methyl]-5-methyl-2,4-dioxo-5-phenyl-1-imidazolidinyl]methyl]-benzamide;
    3-[[3-[[7-(aminoiminomethyl)-2-naphthalenyl]methyl]-5-methyl-2,4-dioxo-5-phenyl-1-imidazolidinyl]methyl]-benzamide;
    7-[[3-[(3-aminophenyl)methyl]-4-methyl-2,5-dioxo-4-phenyl-1-imidazolidinyl]methyl]-2-naphthalenecarboximidamide; and
    7-[[3-[[4-(aminoiminomethyl)phenyl]methyl]-4-methyl-2,5-dioxo-4-phenyl-1-imidazolidinyl]methyl]-2-naphthalene carboximidamide;

as a single stereoisomer, a mixture of individual stereoisomers, or a racemic mixture.

* * * * *